US010073951B2

(12) United States Patent
Mohebbi et al.

(10) Patent No.: US 10,073,951 B2
(45) Date of Patent: Sep. 11, 2018

(54) DEMOGRAPHICALLY FILTERABLE INTERFACE FOR CONVEYING INFORMATION ABOUT A MEDICATION

(71) Applicant: GoodRX, Inc., Santa Monica, CA (US)

(72) Inventors: Matthew Mohebbi, San Francisco, CA (US); Thomas Goetz, San Francisco, CA (US); Adam Baker, San Francisco, CA (US)

(73) Assignee: GoodRx, Inc., Santa Monica, CA (US)

( * ) Notice: Subject to any disclaimer, the term of this patent is extended or adjusted under 35 U.S.C. 154(b) by 634 days.

(21) Appl. No.: 14/746,020

(22) Filed: Jun. 22, 2015

(65) Prior Publication Data

US 2015/0370998 A1 Dec. 24, 2015

Related U.S. Application Data

(60) Provisional application No. 62/016,034, filed on Jun. 23, 2014, provisional application No. 62/098,956, filed on Dec. 31, 2014.

(51) Int. Cl.
*G06F 19/00* (2018.01)
*G16H 10/20* (2018.01)
*G16H 50/70* (2018.01)

(52) U.S. Cl.
CPC ........ *G06F 19/3443* (2013.01); *G06F 19/326* (2013.01); *G16H 10/20* (2018.01); *G16H 50/70* (2018.01)

(58) Field of Classification Search
CPC ............................ G06F 19/326; G06F 19/3443
See application file for complete search history.

(56) References Cited

U.S. PATENT DOCUMENTS 6,014,631 A * 1/2000 Teagarden .......... G06F 19/3456
128/920
2007/0016443 A1 * 1/2007 Wachman ........... G06F 19/3456
705/2

(Continued)

OTHER PUBLICATIONS

PCT International Search Report and Written Opinion, PCT Application No. PCT/US2015/036938, dated Sep. 30, 2015, eleven pages.

*Primary Examiner* — Neal Sereboff
(74) *Attorney, Agent, or Firm* — Fenwick & West LLP

(57) ABSTRACT

A medication analysis system maintains a database of medication profiles for users of medications, each medication profile being associated with a person and includes demographic information about the person and user experience information describing the person's experiences with one or more medications. An input from a user is received that requests information about a medication for a desired demographic. A cluster of medication profiles is identified from the database of medication profiles that include user experience information describing peoples' experiences with the medication. One or more satisfaction metrics are determined for the medication using user experience information in the identified set of medication profiles. A demographically filterable interface is provided to the user device, the interface presenting one or more satisfaction metrics for the particular medication as a function of one or more demographic characteristics of the demographic information of the people associated with the identified medication profiles.

20 Claims, 12 Drawing Sheets

(56) References Cited

U.S. PATENT DOCUMENTS

| | | | |
|---|---|---|---|
| 2007/0136234 A1* | 6/2007 | Levin | G06F 17/30536 |
| 2007/0192134 A1* | 8/2007 | Littenberg | G06Q 10/10 |
| | | | 705/2 |
| 2007/0226009 A1* | 9/2007 | Hicks | G06F 19/328 |
| | | | 705/2 |
| 2008/0195422 A1* | 8/2008 | Nessinger | G06Q 10/00 |
| | | | 705/3 |
| 2010/0280846 A1* | 11/2010 | Clements | G06F 19/3437 |
| | | | 705/2 |
| 2012/0089547 A1* | 4/2012 | Gogolak | G06F 19/704 |
| | | | 706/45 |
| 2014/0052475 A1* | 2/2014 | Madan | G06F 19/3437 |
| | | | 705/3 |
| 2014/0180706 A1* | 6/2014 | Hanley | G06F 19/3431 |
| | | | 705/2 |
| 2015/0169773 A1* | 6/2015 | Woodard | G06F 17/30884 |
| | | | 707/733 |

* cited by examiner

465

Stories about AMBIEN

Filter — 470

From everyone — 482

| ALL |
| Male |
| Female |

| ALL |
| 18-34 |
| 35-54 |
| 55+ |

480 → (2 stories)

Tip
"Usually doesn't help. Been up for hours after taking it. Mind still races, anxiety still high. Doesn't help with staying asleep. Often feel druggy after waking up."

| Bottom line | Used for | How well it worked |
| Not worth it, thinking about stopping | A month or so | ●●○○○○○ |

How big of a hassle
●●○○○○○

👤 19 year old male | Taken for Insomnia (short-term treatment)
average teen with depression/anxiety

Tip
"My primary care doc switched me to Temazepam bc of all the bad press Ambien was getting. Quite honestly I never had any bad reactions or side effects. Ambien worked like a charm but I think docs are a little afraid bc of the hype the side "

| Bottom line | Used for | How well it worked |
| Worth it overall | Two years or more | ●●●●●●● |

How big of a hassle
●○○○○○○

👤 Female | Taken for Insomnia (long-term treatment)
Full-time working mom

810 → Cymbalta (Duloxetine) (Prescription Only)
Basics
You decide what matters most. See how the medication affects.
Pregnancy Alcohol (Food) Kidneys (Liver) Sex  [Get Results] ← 830

805 {
- Personal page
- Basics
- Benefits and tradeoffs
- Alternatives
- Reviews
- Side effects and warnings
- Tips
- Drug facts & package insert
}

Our pharmacists' bottom line
Cymbalta is good for treating depression and anxiety, and may help with chronic pain. More likely than other antidepressants to cause problems if you drink or have high blood pressure.

Men    Women
(37 reviews) (72 reviews) ← 855
[All ages] [18-34] [35-54] [55+] → 820
[All uses ▼] ← 850
(56%) Is it worth it? (64%) ← 860

What to expect with Cymbalta — 835
Taking it for: [Depression ▼]

815 {
[First few hours »] [First few days »] [First few weeks »] [First few months]
Effectiveness
                  Starts working    Full effects  — 845
Common side effects
  [Stomach problems]
  [Headache]
[Drowsiness]
  [Dry mouth]
  [Smaller appetite]
  [Sweating]
— 840
}

825 {
How it works
Improves mood and relieves
Certain kinds of pain.

Cymbalta is a serotonin and norepinephrine reuprake inhibitor (SNRI) antidepressant. It increases serotonin and norepinephrine activity in the brain, which regulates mood.

Drug class
Mental health

Generic available (usually less expensive)
Duloxetine

Used for
Depression
Anxiety
Nerve pain from diabetes
Fibromyalgia
Chronic muscle and joint pain
See off-label uses

Pregnancy safety rating
}

FIG. 8

DEMOGRAPHICALLY FILTERABLE INTERFACE FOR CONVEYING INFORMATION ABOUT A MEDICATION

CROSS-REFERENCE TO RELATED APPLICATIONS

This application claims priority to U.S. Provisional Application No. 62/016,034, filed Jun. 23, 2014, and U.S. Provisional Application No. 62/098,956, filed on Dec. 31, 2014, both of which are incorporated by reference in their entirety.

BACKGROUND

Field of Disclosure

This disclosure relates to the field of data visualization generally, and specifically to analyzing effects of medications on users of varying demographic backgrounds, and presenting results of the analysis to users using demographically filterable interfaces that allow users to filter the results presented using one or more demographic characteristics.

Description of the Related Art

Large sections of the population routinely take medication, and the medication may be prescribed by a doctor or sold to consumers directly without a prescription (i.e., over-the-counter medication). The effects of a medication, both positive and negative, can vary significantly based on a user's demographic characteristics (e.g., age, gender, etc.). Online drug reference guides make available general information about medications, and in some cases reviews of medications. However, general information about a medication, while informative, may not have the same value to a viewing user as actual experiences of users of the medication who have similar demographic backgrounds as the viewing user. Moreover, current online drug reference guides simply present a listing of reviews without ways to filter out reviews from users of dissimilar demographics.

SUMMARY

A medication analysis system maintains a database of medication profiles for users of medications, each medication profile is associated with a person and includes demographic information about the person and user experience information describing the person's experiences with one or more medications. The information in the medication profiles are obtained directly from users of the medication analysis system or from survey service providers who survey various Internet users for their experiences with the medication and/or for demographic information.

The medication analysis system receives from a user device an input from a user, the input requests information about a medication for a desired demographic of users of the medication. For example, the user may request information on the medication AMBIEN®. The medication analysis system identifies a cluster of medication profiles from the database of medication profiles that include user experience information describing experiences with the medication. The medication analysis system identifies a set of medication profiles within the cluster that have demographic information that matches the desired demographic of users of the medication.

The medication analysis system determines one or more satisfaction metrics for the medication using user experience information in the identified set of medication profiles. A satisfaction metric is a measure of one or more medication users' satisfaction with using a medication. Satisfaction metrics are derived from information in medication profiles of people who have experience with the medication. For example, a satisfaction metric may include: a performance distribution relating to hassle of taking the medication, a performance distribution relating to the effectiveness of the medication, a performance distribution relating to the overall worth of taking the medication, one or more stories about the medication, and side effects information for the medication, or some combination thereof.

The medication analysis system provides to the user device a demographically filterable interface. The demographically filterable interface presents the one or more satisfaction metrics for the particular medication as a function of one or more demographic characteristics of the people associated with the identified medication profiles. The medication analysis system provides the demographically filterable interface as part of different webpages. In some embodiments, the medication analysis system provides the demographically filterable interface as part of, for example, a medication overview webpage, a tradeoff webpage that presents information describing how people feel about the medication when compared to one or more alternative medications, a real life web page that presents information describing peoples' experiences with the medication outside of a clinical context, a side effects web page presenting side effects information for the medication, or some combination thereof.

In some embodiments, the medication analysis system generates insights about a medication using the medication profiles. The medication analysis system conducts an ongoing analysis of the medication profiles to ascertain common behaviors or attributes that a certain medication user segment has in common, given a particular effectiveness rating of the medication. These common behaviors and/or attributes are insights into why the user segment provides the medication with the particular effectiveness rating. The medication analysis system may include these insights as part of an interface provided to the user device.

BRIEF DESCRIPTION OF DRAWINGS

FIG. 4B illustrates an example demographically filterable interface presenting story information presented on the real life webpage of FIG. 4A according to an embodiment.

FIG. 8 illustrates another example of a user interface displayed by a user device showing a medication overview webpage according to an embodiment.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures and may indicate similar or like functionality.

System Overview

Figure 1:
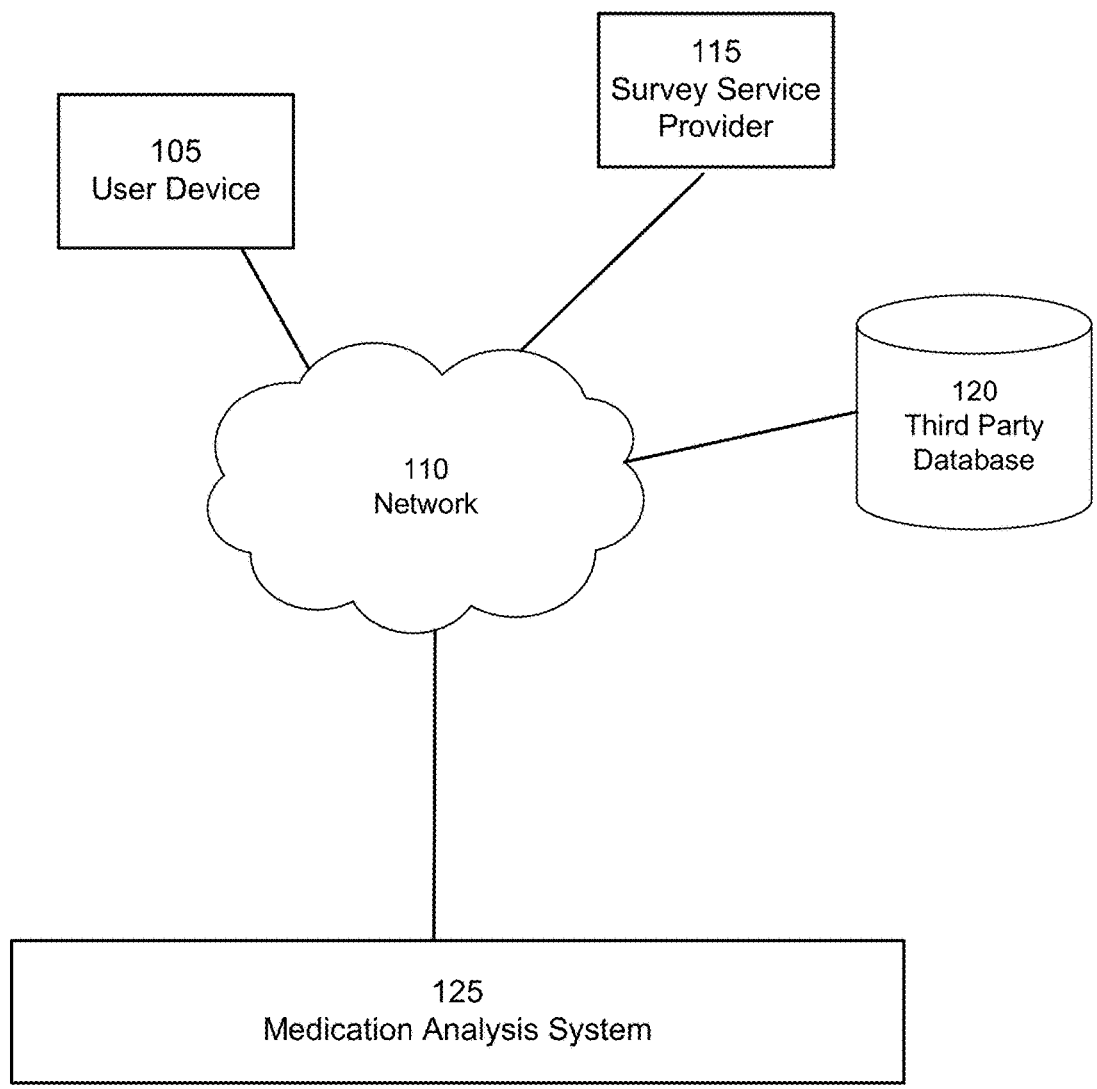
FIG. 1 is a high-level block diagram illustrating an embodiment of a medication analysis system connected by a network to a user device, a survey service provider, and a third party database according to one embodiment.

FIG. 1 is a high-level block diagram illustrating an embodiment of a medication analysis system 125 connected by a network 110 to a user device 105, a survey service provider 115, and a third party database 120. Here only one user device 105, survey service provider 115, third party database 102, and medication analysis system 125 are illustrated but there may be multiple instances of each of these entities. For example, there may be thousands or millions of user devices 105 in communication with multiple medical monitoring systems 115, survey service providers 115, and third party databases 120.

The network 110 provides a communication infrastructure between the user device 105, the survey service provider 115, the third party database 120, and the medication analysis system 125. The network 110 is typically the Internet, but may be any network, including but not limited to a Local Area Network (LAN), a Metropolitan Area Network (MAN), a Wide Area Network (WAN), a mobile wired or wireless network, a private network, or a virtual private network.

The survey service provider 115 is an entity (e.g., GOOGLE® CONSUMER SURVEYS) that conducts surveys for Internet users. The surveys include medication surveys that request the user describe their experiences with one or more medications. The survey service provider 115 maintains some demographic information about Internet users. The survey service provider 115 receives one or more targeting criteria used to identify a target group of Internet users for a medication survey and survey questions from the medication analysis system 125. The survey questions may ask for user experience information and/or for one or more demographic characteristics of the user. User experience information is information describing that person's experiences. User experience information may include, e.g., whether a user has used a particular medication, how much of a hassle it was to use the medication, the effectiveness of the medication, the length of time the medication was taken, what employment medical insurance plan (including medication coverage) and/or employment dental insurance plan is used by the user, what the user's co-pay was for the medication, what side-effects the user had while on the medication, any tips regarding the use of the medication, was the medication overall worth taking, the user for one or more demographic characteristics about the user, any tips about the medication, some other information relating to the user's experience with the medication, or some combination thereof.

The targeting criteria identify one or more desired demographic characteristics of users to receive the medication survey. Demographic characteristics are types of information that may be used to characterize a user as being a part of a particular subset of a population. A demographic characteristic may be, for example, biographic and other types of descriptive information, exercise activity level, type of employment, employment medical insurance plan (including medication coverage), employment dental insurance plan, co-pay amounts for medication, health descriptors (e.g., diet, exercise level, smoker/nonsmoker, medication allergies, etc.), educational history, gender, ethnicity, location, or other medical information associated with the user, or some combination thereof. The demographic characteristics about a user are collectively referred to as demographic information.

The survey service provider 115 identifies Internet users associated with the requested targeting criteria, also known as a target group of users, and surveys the identified users using the one or more questions. For example, the survey service provider 115 may survey the target group of users using "soft paywall" for websites offering premium content, such that users visiting these websites have the option of responding to a survey to access content for free. The survey service provider 115 collects responses from users of the target group of users and provides the collected responses, referred to as survey information, to the medication analysis system 125.

The third party database 120 comprises computer servers that host prescription information associated with one or more medications. Prescription information describes medication prescribed by a medical doctor or medication that may be obtained without a prescription (i.e., over-the-counter medication). Prescription information includes clinical pharmacology, indications and usage (i.e., uses/indications for which the drug has been approved by the responsible entity), contraindications (i.e., situations where the medication should not be used), warnings (i.e., possible serious side effects when used alone or with other identified medications), precautions, adverse reactions (i.e., all side effects when used alone or in combination with other medications—including those in the warnings section), drug abuse and dependence (i.e., discusses whether there is a risk of dependence), over dosage (i.e., gives results of overdose and provides recommended actions), dosage and administration (e.g., size of dose and when to take), physical data (e.g., physical characteristics—shape, color, imprint, size, etc.), characteristic information (e.g., information used to identify a medication), a manufacturer of the medication, a brand name of the medication, a generic name of the medication, a description of the medication, an image of the medication (e.g., standard image data), some other information about the medication, or some combination thereof. In some embodiments, the third party database 120 may be controlled by an entity responsible for determining the requirements of package inserts for medication (e.g., in the U.S., this is controlled by the Food and Drug Administration). The third party database 120 may directly provide prescription information to the user device 105 via the network 110, or the third party database 120 may provide prescription information or portions of prescription information to the medication analysis system 125, and the prescription information may be made available to the user device 105 from the medication analysis system 125.

The user devices 105 are computing devices that execute computer program modules—e.g., a web browser or other client application—which allow a user to interact with the medication analysis system 125, and generally browse the Internet. A user device 105 might be, for example, a personal computer, a tablet computer, a smart phone, a laptop computer, or other type of network-capable device such as a networked television or set-top box.

The medication analysis system 125 maintains a database of medication profiles. Each medication profile is associated with a user of one or more medications and includes demographic information about the user and user experience information describing that user's experiences with the one or more medications. The medication analysis system 125 receives survey information associated with various Internet users from the survey service provider 115. Additionally, in some embodiments, the medication analysis system may receive survey information directly from a user of the medication analysis system 125. The medication analysis system 125 generates medication profiles based on the received survey information.

The medication analysis system 125 provides a user interface to the user device 105 that allows a user of the user device 105 to request information about a medication. Responsive to receiving the request, the medication analysis system 125 generates one or more satisfaction metrics for the medication. A satisfaction metric is a measure of one or more medication users' satisfaction with using a medication (e.g., a performance distributions relating to hassle of taking the medication, performance distributions relating to the effectiveness of the medication, stories about the medication, side effects information for the medication, etc.). Satisfaction metrics are derived from information in medication profiles of people who have experience with the medication, specifically, the satisfaction metrics are generated using a cluster of medication profiles or a subset thereof, that include user experience information pertaining to the medication.

The medication analysis system 125 generates a user interface that includes one or more demographically filterable interfaces. A demographically filterable interface is a user interface which presents one or more satisfaction metrics for a medication to a user as a function of one or more selectable demographic characteristics. The user interface provides to the user device 105 one or more demographically filterable interfaces. A user may filter what medication profiles are used to generate the one or more satisfaction metrics being presented by the demographically filterable interface by selecting one or more desired demographic characteristics (e.g., gender, age, etc.). A selection of one or more demographic characteristics causes the medication analysis system 125 to identify a set of medication profiles within the cluster of medication profiles having the same demographic characteristics as the desired demographic characteristics. The medication analysis system 125 updates the satisfaction metric based on the identified set of medication profiles, and provides the updated satisfaction metric to the user device 105.

The medication analysis system 125 may also generate interfaces using prescription information received from one or more third party databases 120. For example, the medication analysis system 125 may generate an interface that presents information from the package insert of the medication, warnings about the medication, common side effects of the medication reported during clinical trials.

In some embodiments, the medication analysis system 125 may include on the same webpage a demographically filterable interface as the interface generated using the prescription information. For example, a webpage might present common side effects of the medication reported during clinical trials and a demographically filterable interface displaying side effects of the medication reported listed in the medication profiles. Accordingly, a user is able to easily compare how side effects experienced by medication users of a desired demographic makeup compare to the side effects reported for the medication during clinical trials.

In some embodiments, the generated interface may be a cost webpage that identifies whether, given a particular co-pay, it is cheaper to purchase a medication or a generic version of the medication. Moreover, the cost web-page also identifies how the medication should be purchased (e.g., using insurance or not using insurance). An example, of a cost webpage is discussed below with reference to FIG. 7.

The medication analysis system 125 conducts an ongoing analysis of the medication profiles to ascertain common behaviors or attributes that certain user segments have in common. For instance, users who rate a medication as "worth it" (highly effective/little or no hassle) might commonly take it with milk, or users who rate a medication as "not worth it" (not effective/much hassle) might all have been taking it for a year or longer, etc. The medication analysis system 125 may present these insights as part of the generated user interfaces.

Interactive Graphical User Interface

The medication analysis system 125 provides a homepage that is presented to a user of a user device 105 via, e.g., a browser. The medication analysis system 125 receives from a user device 105 an input from a user that requests information about a particular medication (also referred to as a subject medication). For example, a user may request information on the medication AMBIEN®. FIGS. 2-7 are some examples of user interfaces that may be presented to a user in response to receiving an input that requests information about the medication AMBIEN®. FIG. 8 is another example user interface that may be presented to a user in response to a request for information.

Figure 2:
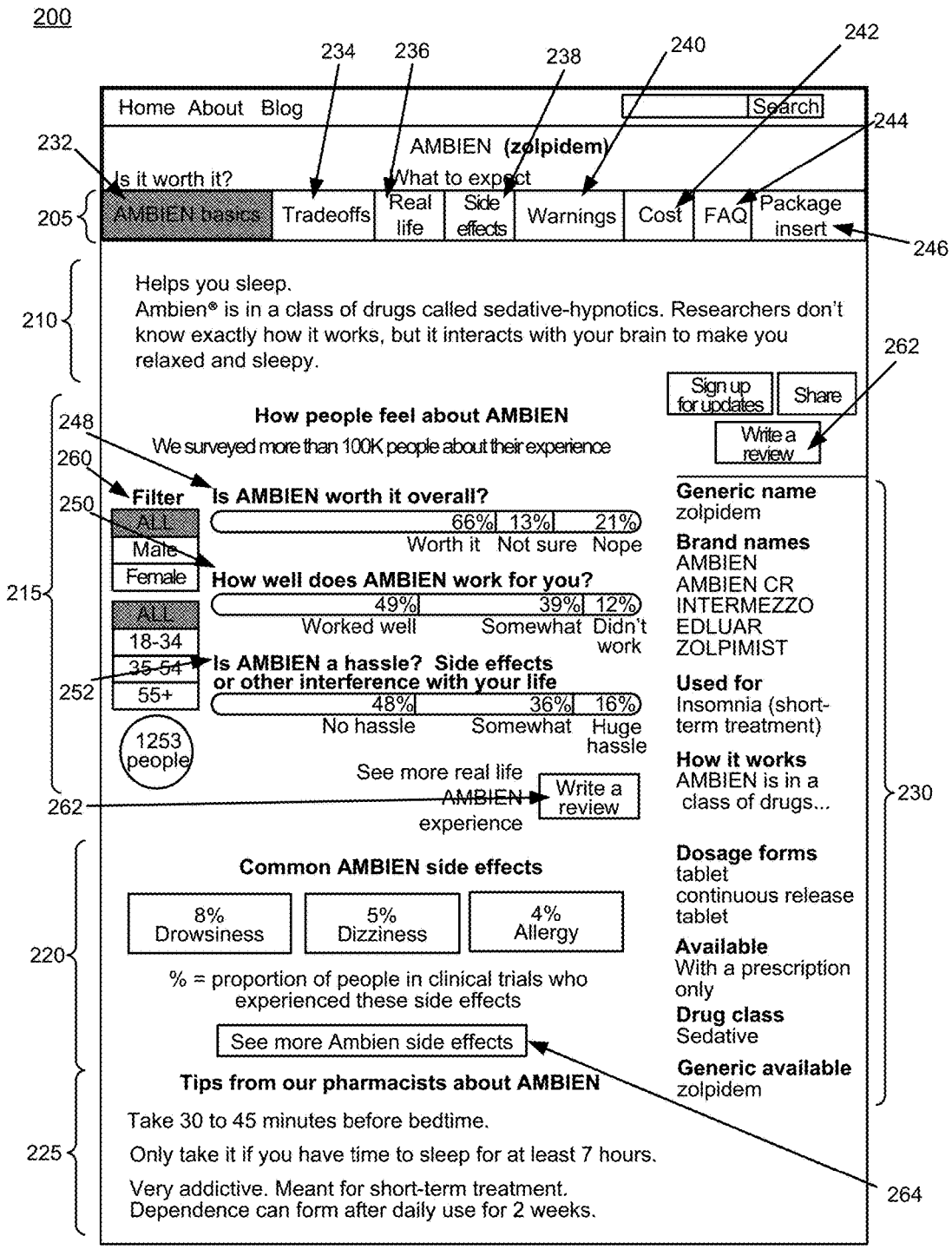
FIG. 2 illustrates an example of a user interface displayed by a user device showing a medication overview webpage according to an embodiment.

FIG. 2 illustrates an example of a user interface 200 displayed by the user device 105 showing a medication overview webpage according to an embodiment. The user interface 200 includes a main menu 205, an overview section 210, a demographically filterable interface 215, a side effect section 220, a pharmacist tip section 225, and a miscellaneous information section 230. The main menu 205 includes a plurality of selectable navigation buttons that allow a user to navigate to other pages associated with the subject medication (e.g., AMBIEN®). In this embodiment, the navigation buttons include a medication basics (i.e., AMBIEN® basics) button 232, a tradeoffs button 234, a real life button 236, a side effects button 238, a warnings button 240, a cost button 242, a frequently asked questions (FAQ) button 244, and a package insert button 246. In other embodiments, the main menu 205 may include one or more different navigation buttons than those described herein or may only include a subset of those navigation buttons. Similarly, the functions of the navigation buttons can be distributed among the navigation buttons and/or combined in a different manner than is described here.

In this embodiment, the medication basics button 232 is selected, accordingly, the user interface 200 presents the medication overview webpage shown in FIG. 2. If the user selects a different navigation button, the user interface 200 presents a different webpage. FIGS. 3-7 discussed below illustrate different webpages that correspond to selections of navigation buttons 234, 236, 238, 240, and 242. The FAQ button 244, if selected, causes the user interface 200 to present a webpage that lists FAQs for the subject medication. The package insert button, 246, if selected, causes the user interface 200 to present package insert information received from the FDA for the subject medication.

The overview section 210 provides a short description of the subject medication. For example, the overview section 210 may describe why it is commonly used, how the medication is generally categorized (e.g., opiate, sedative, etc.), how the medication works, etc.

The demographically filterable interface 215 presents a plurality of satisfaction metrics as a function of demographic information. In this embodiment, the demographically filterable interface 215 includes three satisfaction metrics that are different types of performance distributions, an overall worth performance distribution 248, an effectiveness performance distribution 250, and a hassle performance distribution 252. Each performance distribution 248, 250, 252 is generally divided into a plurality of levels of satisfaction, and presents results as a function of demographic information. For example, the overall worth performance distribution 248 presents what percentage of users indicated that the medication was worth using, what percentage of users were not sure whether the medication was worth using, and what percentage of users indicated that the medication was not worth using. The effectiveness performance distribution 250 presents what percentage of users indicated that the medication worked well, what percentage of users indicated that medication worked somewhat, and what percentage of users indicated that the medication did not work. The hassle performance distribution 252 presents what percentage of users indicated that the medication was not hassle to use, what percentage of users indicated that medication was somewhat of a hassle to use, and what percentage of users indicated that the medication was a huge hassle to use.

In this embodiment, the demographically filterable interface 215 includes a demographic filter 260. The demographic filter 260 allows a user to filter the data presented by the satisfaction metrics 248, 250, 252. In this example, the ALL button is selected for both gender and age ranges, accordingly, the results presented by the performance distributions 248, 250, 252 are for the entire set of people who reported using AMBIEN® (i.e., their medication profiles include user experience information indicating they had used AMBIEN®). In this embodiment, a user may narrow the sample set to a particular demographic makeup by, e.g., selecting a particular gender and/or age range, such that results presented by the performance distributions 248, 250, 252 correspond to data associated with users of the particular demographic makeup. Accordingly, a user of a particular demographic makeup, e.g., 50 year old female, may dynamically filter the results presented by the performance distributions 248, 250, 252 to see how satisfied others of her demographic makeup were with the subject medication (e.g., AMBIEN®).

The user interface 200 includes one or more review buttons 262. The review button 262, if selected, presents a form interface to the user asking for some demographic information about the user and some user experience information that describes that user's experiences with the subject medication. For example, the form interface may request age of the user, gender of the user, a brief description of the user (e.g., How would you describe yourself?), information describing why the user is taking the subject medication, a length of time the user has been taking the subject medication, some other demographic information, some other information describing the user's experience with the subject medication, or some combination thereof. The information received from the user via the form interface is stored by the medication analysis system 125 as a medication profile in the database of medication profiles used to generate the performance distributions 248, 250, 252 in FIG. 2, as well as, e.g., other satisfaction metrics described below with regard to FIGS. 3A, 3B, 4A, and 4B.

In some embodiments, when a user enters their own experience through a form interface, the medication analysis system 125 may add an indicator to one or more of the displayed satisfaction metrics to reflect where the user falls in the aggregated information. In this way a user can put themselves "on the map" alongside other users.

Figure 5:
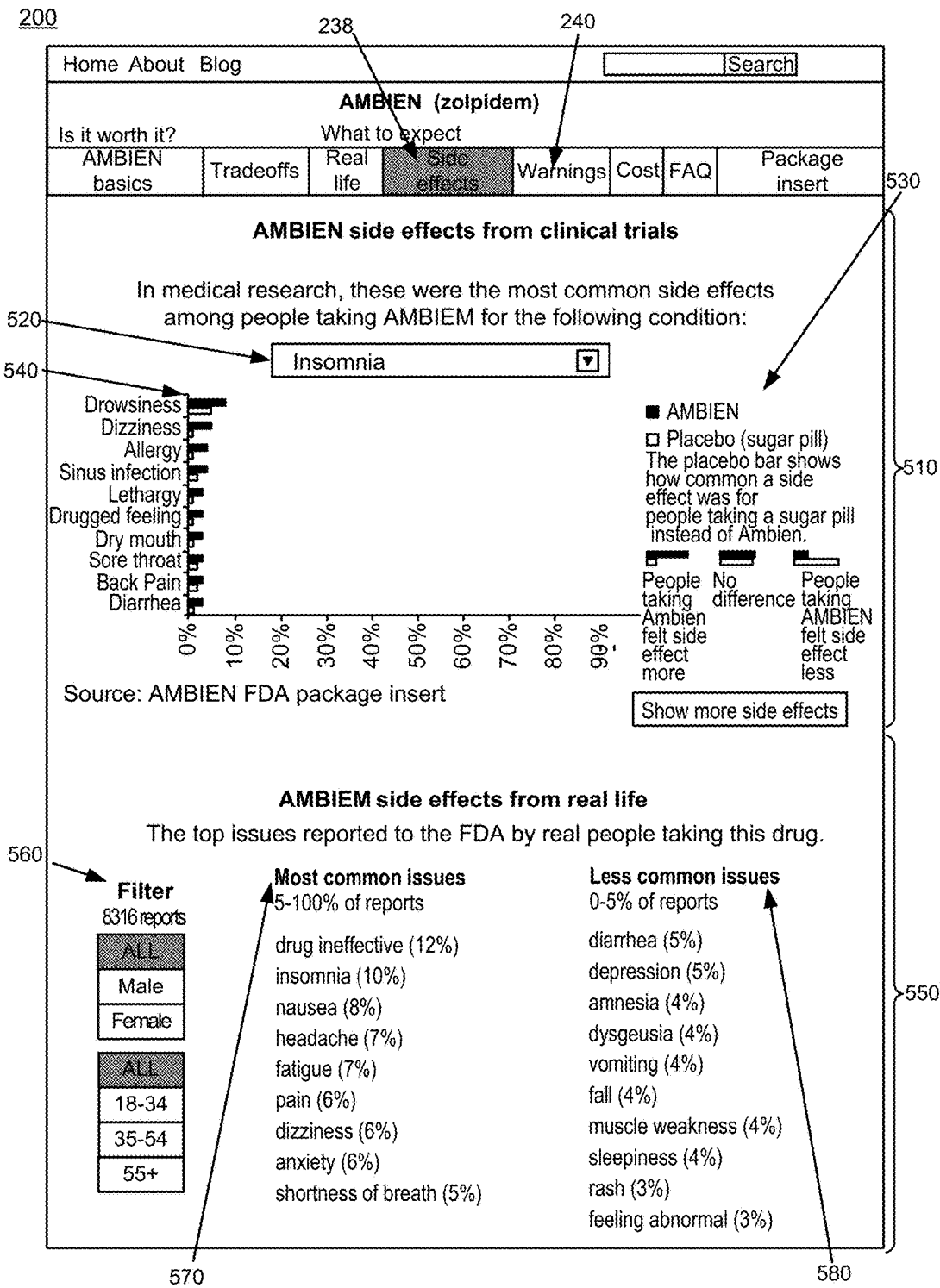
FIG. 5 illustrates an example of the user interface of FIG. 2 displayed by a user device showing a side effects webpage according to an embodiment.

The side effect section 220 presents to the user common side effects of the subject medication. For example, given the entire sample set of people who reported using AMBIEN® during the clinical trials, the top side effects are drowsiness, dizziness, and allergy. The side effect section 220 includes a side effect button 264 that if selected, causes the user interface 200 to present a side effects web page as shown in FIG. 5.

The pharmacist tip section 225 displays one or more tips from pharmacists for the subject medication. A tip may generally be anything relating to the medication. Some types of tips are e.g., when to take the medication, warnings regarding addictiveness for the medication, common side effects, etc.

The miscellaneous information section 230 displays various information about the subject medication. For example, the miscellaneous information section 230 may include a generic name for the medication, brand names for the medication, what the medication is used for, how the medication works, dosage forms, whether a prescription is needed or not needed, drug class for the medication, possible generic alternatives to the medication, some other information associated with the medication, or some combination thereof.

Figure 3A:
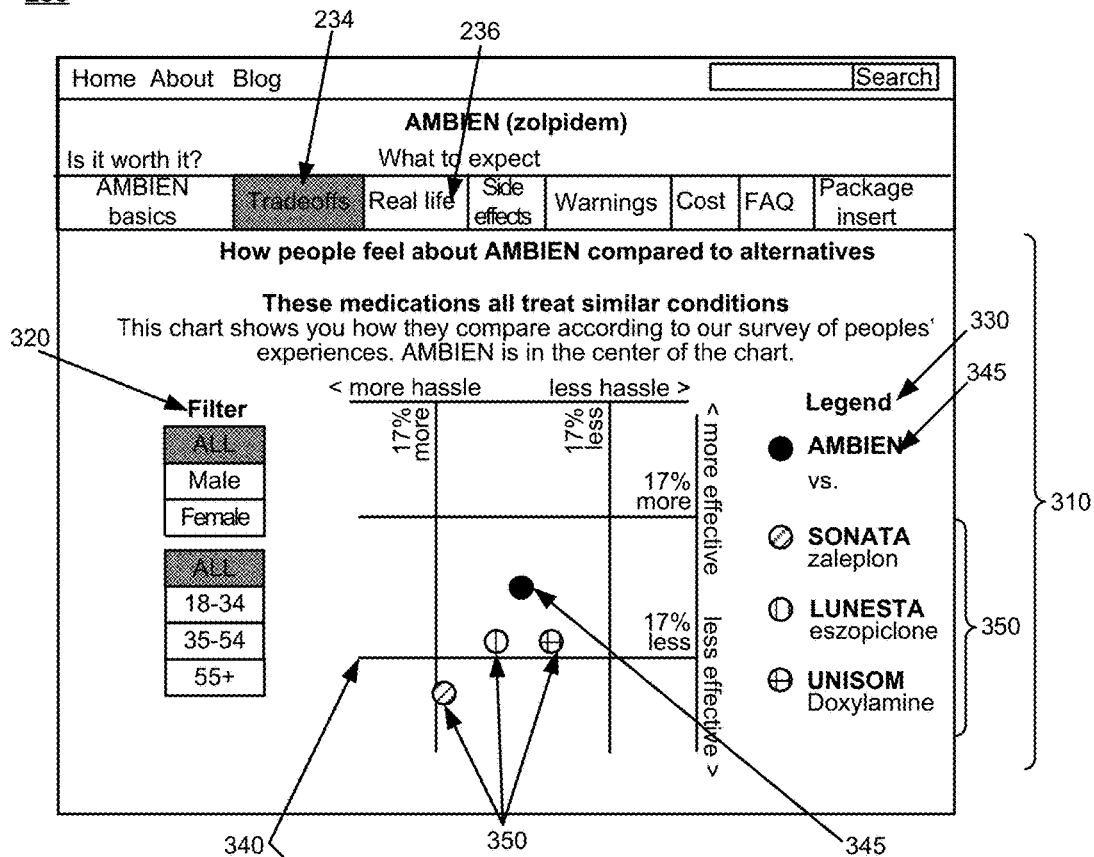
FIG. 3A illustrates an example of the user interface of FIG. 2 displayed by a user device showing a tradeoff webpage according to an embodiment.

After the tradeoffs button 234 is selected, the user interface 200 presents a tradeoff webpage shown in FIG. 3A. FIG. 3A illustrates an example of the user interface 200 displayed by the user device 105 showing the tradeoff webpage according to an embodiment. The tradeoff webpage presents information describing how people feel about the subject medication when compared to alternatives. The tradeoff webpage includes a demographically filterable interface 310 that compares users' satisfaction with other medications used to treat similar conditions with the users' satisfaction with the subject medication. The demographically filterable interface 310 includes a demographic filter 320, a legend 330, and a graph 340.

The demographic filter 320 allows a user to filter the data presented by the graph 340. The demographic filter 320 is substantially similar to the demographic filter 260 described above with regard to FIG. 2. In this embodiment, the ALL button is selected for both gender and age ranges, accordingly, the results presented by graph 340 are for the entire set of people who reported using AMBIEN® (i.e., their medication profile includes user experience information indicating they had used AMBIEN®). The legend 330 lists a subject medication 345 along with possible alternative medications 350 to the subject medication.

The graph 340 presents satisfaction metrics as a function of demographic information for the medications 350. In this embodiment, the demographically filterable interface 215 includes two satisfaction metrics, an effectiveness performance distribution and a hassle performance distribution, which make up the vertical and horizontal axes, respectively, of the graph 340. The graph 340 presents the satisfaction metrics for the medications 350 relative to the subject medication 345. For example, over the entire set of medication profiles including user experience information for SONATA®, the graph indicates that it is more of a hassle to use and less effective than AMBIEN®. A user may filter the data used to generate the satisfaction metrics by selecting one or more demographic characteristics using the demographic filter 320. For example, a user may narrow the data set to users of a particular demographic makeup by, e.g., selecting a particular gender and/or age range, such that results presented by the satisfaction metrics correspond to data associated with users of the particular demographic makeup.

Figure 3B:
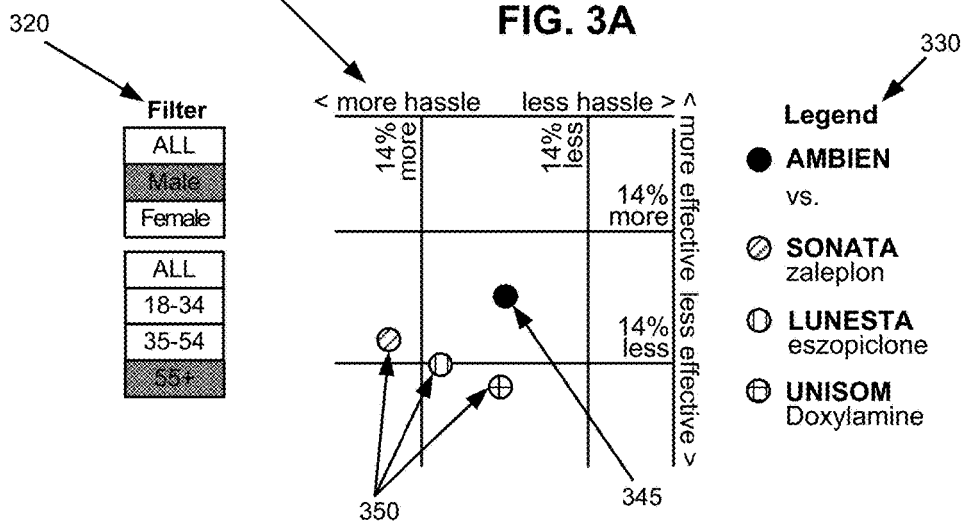
FIG. 3B illustrates a demographically filterable interface of FIG. 3A for a different demographic makeup according to an embodiment.

FIG. 3B illustrates the demographically filterable interface 310 of FIG. 3A for a different demographic makeup according to an embodiment. In this embodiment, the data set has been narrowed to users who are male and over 55 years old. Accordingly, the medications 350 are presented in locations determined from user experience information of medication profiles having demographic information indicating they are males who are over 55 years of age. Users of this demographic makeup, for example, indicate that SONATA® is still more of a hassle to use than AMBIEN®, and while still less effective than AMBIEN® is considered by this demographic makeup to be more effective than the effectiveness attributed to SONATA® shown in FIG. 3A. The medication 345 is presented in the middle of the graph 340 in both FIGS. 3A and 3B, because the satisfaction metrics for the medications 350 are presented relative to the subject medication 345, accordingly, the location of the subject medication 345 does not move as a function of demographic makeup.

In some embodiments (not shown), the tradeoff webpage may include information describing the upsides and downsides of the subject medication. For example, the tradeoff webpage may present an upside of AMBIEN® as helping people fall asleep and a downside as being potentially addictive. Additionally, in some embodiments, the tradeoff webpage may include a bottom line that provides a summary of one or more of the upsides and/or downsides. For example, the bottom line information for AMBIEN® may be that it is good for falling asleep and staying asleep, but it can be habit forming and might be more likely than other sleep medicines to cause disturbing side effects. Additionally, in some embodiments, the tradeoff webpage may list one or more alternative medications to the subject medications. One or more of the listed alternatives may also be the medications 350 in the interaction interface 310.

Figure 4A:
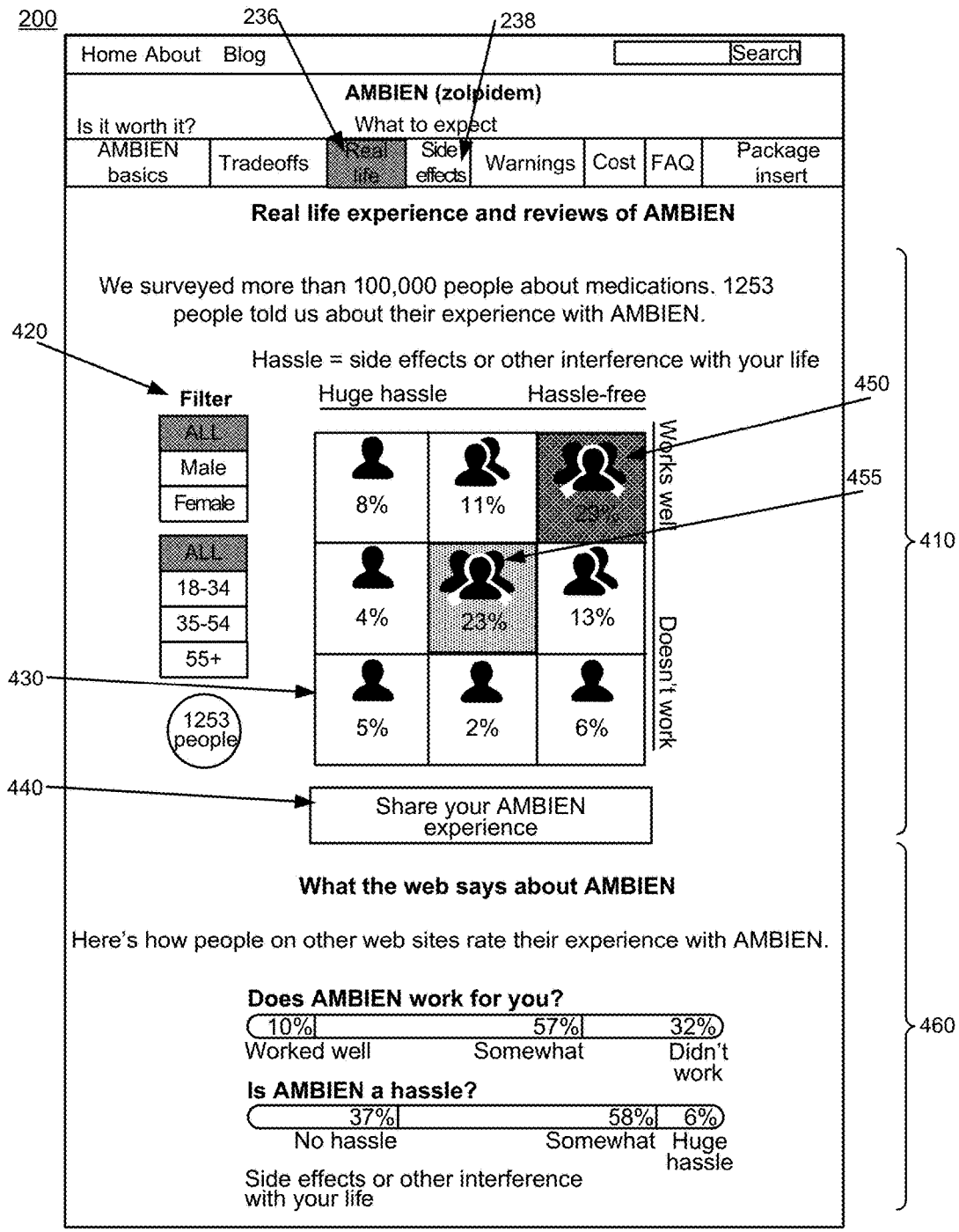
FIG. 4A illustrates an example of the user interface of FIG. 2 displayed by a user device showing a real life webpage according to an embodiment.

After the real life button 236 is selected, the user interface 200 presents a real life webpage shown in FIGS. 4A and 4B. FIG. 4A illustrates an example of the user interface 200 displayed by the user device 105 showing a real life webpage according to an embodiment. The real life webpage presents information describing peoples' experiences with the subject medication outside of a clinical context. The real life webpage includes a demographically filterable interface 410 that presents a plurality of satisfaction metrics in a grid format for the subject medication. In this embodiment, satisfaction is measured using two satisfaction metrics, specifically a hassle performance distribution and an effectiveness performance distribution.

The demographically filterable interface 410 includes a demographic filter 420, a graph 430, and a review button 440. The demographic filter 420 allows a user to filter the data presented by the graph 430. The demographic filter 420 is substantially similar to the demographic filter 260 described above with regard to FIG. 2. In this embodiment, the ALL button is selected for both gender and age ranges, accordingly, the results presented by graph 420 are for the entire set of people who reported using AMBIEN® (i.e., their medication profile includes user experience information indicating they had used AMBIEN®). In this embodiment, a user may narrow the sample set to a particular demographic makeup by, e.g., selecting a particular gender and/or age range, such that results presented by the graph 430 correspond to data associated with users of the particular demographic makeup.

The graph 430 presents surveyed users' satisfaction with the subject medication based on the selected demographic characteristics. The graph 430 is divided up into nine sections where each section is associated with a particular amount of hassle and a particular amount of effectiveness. In some embodiments, one or more of the sections are emphasized to reflect what percentage of surveyed users described by the demographic makeup selected via the demographic selection interface 420 are associated with each section. For example, section 450 is associated with the largest number of surveyed users and is shaded differently than section 455 which is associated with the second largest percentage of surveyed users.

The review button 440 is substantially similar to the review button 262 described above with regard to FIG. 2. In some embodiments, after the review button 440 is selected, a form interface is presented, and the user enters their own experience through the form interface, the medication analysis system 125 may add an indicator to the graph 430 that reflects where the user falls in the information being presented.

Additionally, in some embodiments, a user may click on or place their cursor above a particular section in the graph 430 to see additional information about the medication profiles associated with that section. Additional information might include, e.g., one or more stories about the medication generated from medication profiles associated with the particular section.

The real life webpage includes an other website data section 460. The other website data section 460 presents user satisfaction with the subject medication based on data retrieved from other websites (e.g., the third party database 120). In the other website data section 460 user satisfaction is based on two satisfaction metrics, specifically, effectiveness and hassle. Thus, the real life webpage allows a user to compare the satisfaction of people in an uncontrolled environment (e.g., from user experience information in the medication profiles) about the effectiveness of the subject medication with for example, clinical data received from the Food and Drug Administration (FDA) about the subject medication.

The real life webpage may be scrolled to display other information like, for example, a demographically filterable interface that presents story information. For example, FIG. 4B illustrates an example demographically filterable interface 465 presenting story information presented on the real life webpage of FIG. 4A according to an embodiment. The demographically filterable interface 465 includes a demographic filter 470 and one or more stories 475. The demographic filter 470 allows a user to filter which stories 475 are presented by selecting particular demographic characteristics. The demographic filter 470 is substantially similar to the demographic filter 260 described above with regard to FIG. 2. In this embodiment, the ALL button is selected for both gender and age ranges, accordingly, the stories 475 presented are generated using all medical profiles associated with users who reported using AMBIEN® and submitted a tip. In this embodiment, where only two users had submitted a tip, the medication analysis system 125 generates stories using medical profiles associated with the two users, and the demographically filterable interface 465 presents both stories, specifically story 482 and story 484. Each of the stories 475 includes fields populated by some demographic information about the user and some user experience information relating to the subject medication. For example, the stories 482,484 include a tip from the user that is associated with the subject medication, satisfaction metrics describing the medication user's satisfaction with the subject medication, the age of the user associated with the story, the reason the subject medication was taken, how long the subject medication was used, and some information about the user.

A user may narrow the set of medication profiles used to generate stories to those having a particular demographic makeup by, e.g., selecting a particular gender and/or age range, such that stories 475 presented correspond to data associated with users of the particular demographic makeup. For example, if "Female" was selected on the demographic filter 470, only the story 484 would be presented, because there are only two stories for the entire set of medication profiles including user experience information for the subject medication.

After the side effects button 238 is selected, the user interface 200 presents a side effects webpage shown in FIG. 5. FIG. 5 illustrates an example of the user interface 200 displayed by the user device 105 showing a side effects webpage according to an embodiment. The side effects webpage includes a clinical interface element 510 that presents side effects reported during clinical trials as a function of a condition being treated by the subject medication. The clinical interface element 510 includes a condition menu 520, a legend 530, and a clinical side effects graph 540. The condition menu 520 is a drop down menu that includes one or more possible conditions. For example, clinical trial data for AMBIEN® may include insomnia and insomnia for people over 60 years of age as selectable conditions. The legend 530 indicates what data in the clinical side effects graph 540 was reported for people taking the subject medication and what data in the clinical side effects graph 540 was reported for people taking a placebo. The legend 530 also includes information showing how to interpret the data.

The clinical side effects graph 540 presents clinical side effects based on clinical trial information within the FDA package insert for the subject medication. The clinical side effects graph 540 presents one or more side effects (e.g., drowsiness, dizziness, etc.) as a function of the percentage of people who reported having them in the clinical trials. For each side effect, the clinical side effects graph 540 also presents what percentage of people in the clinical trial reported having a particular side effect while using a placebo instead of the subject medication.

The side effects webpage includes a demographically filterable interface 550 that presents side effects information extracted from medication profiles associated with people taking the subject medication. The demographically filterable interface 550 includes a demographic filter 560, a listing of the most common side effects 570 reported to the FDA, and a listing of less common issues 580 reported to the FDA.

The demographic filter 560 allows a user to filter the listings 570, 580 to display side effects of the medication reported for people of a particular demographic makeup. The demographic filter 560 is substantially similar to the demographic filter 260 described above with regard to FIG. 2. In this embodiment, the ALL button is selected for both gender and age ranges, accordingly, the side effects presented in the listings 570, 580 are for the entire set of people. In this example, there are 8316 reports which can be filtered using the demographic filter 560. For example, if "Male" is selected in the demographic filter 560, the listings 570, 580 are updated to include only side effects reported by males. Accordingly, the demographically filterable interface 550 is able to present to a user, side effect information that is targeted to the demographics of that user.

Figure 6:
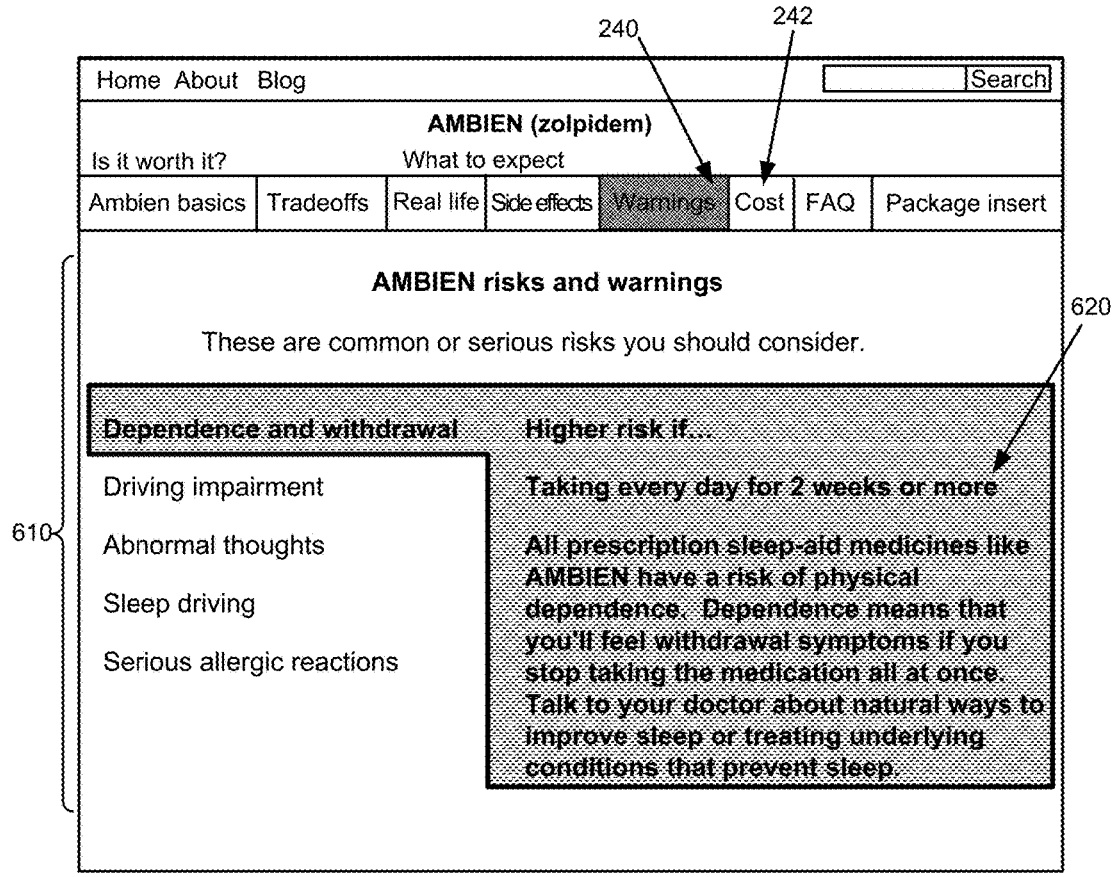
FIG. 6 illustrates an example of the user interface of FIG. 2 displayed by a user device showing a warnings webpage according to an embodiment.

After the warnings button 240 is selected, the user interface 200 presents a warnings webpage as shown in FIG. 6. FIG. 6 illustrates an example of the user interface 200 displayed by the user device 105 showing a warnings webpage according to an embodiment. The warnings webpage includes a warnings interface 610 that presents risks and/or warnings associated with the subject medication. For example, the warnings interface 610 lists dependence and withdrawal, driving impairment, abnormal thoughts, sleep driving, and serious allergic reactions as warnings and/or risks for AMBIEN®. If a particular warning or risk is selected, the warning interface 610 presents additional information associated with selected warning or risk. For example, in FIG. 6 the risk dependence and withdrawal is selected, and additional information 620 is presented by the user device 105.

Figure 7:
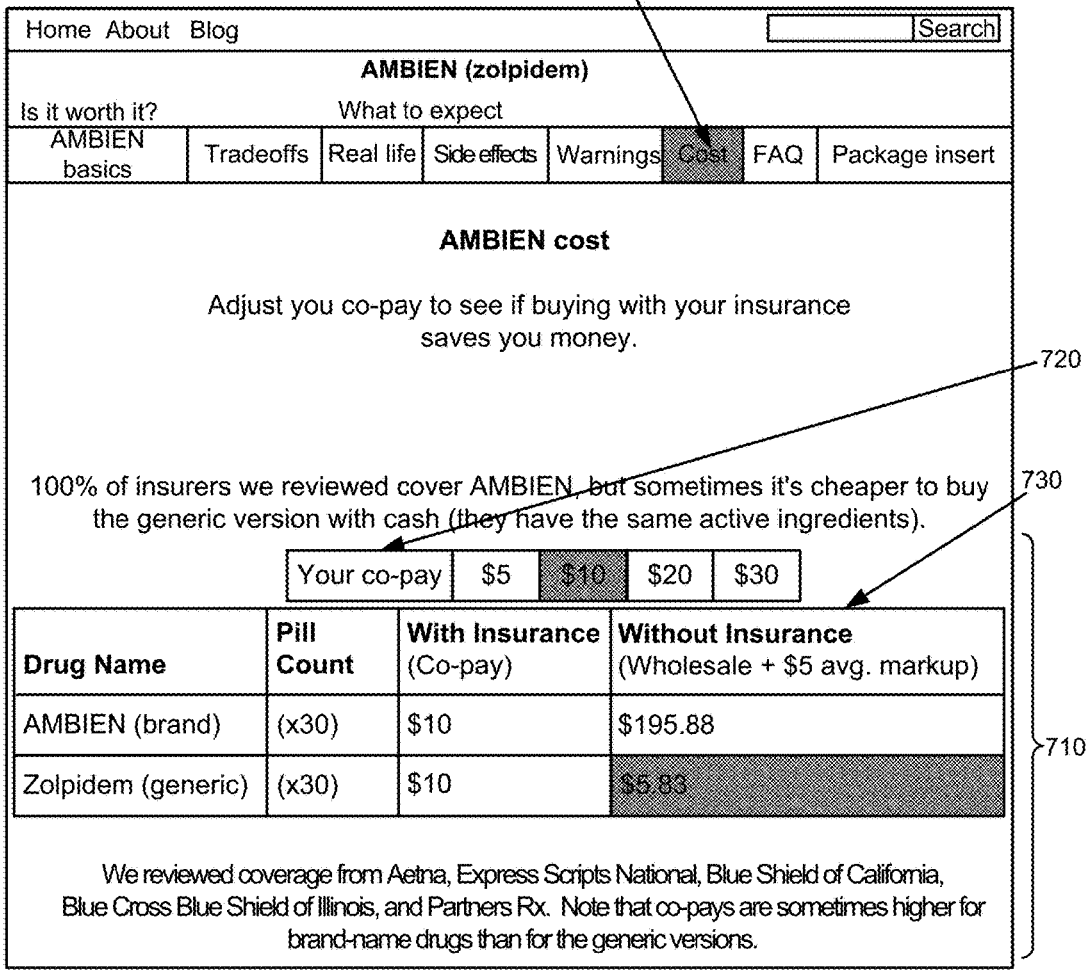
FIG. 7 illustrates an example of the user interface of FIG. 2 displayed by a user device showing a cost webpage according to an embodiment.

After the cost button 242 is selected, the user interface 200 presents a cost webpage as shown in FIG. 7. FIG. 7 illustrates an example of the user interface 200 displayed by the user device 105 showing a cost webpage according to an embodiment. In some instances it is actually cheaper to buy a generic version of a brand name drug. The cost webpage is used to determine whether buying a medication and/or a generic version of the medication is cheaper, and whether the purchase should be made using insurance or not using insurance. The cost webpage includes a cost interface 710 that presents the cheapest method by which a user can obtain the subject medication and/or a generic version of the subject medication. The cost interface 710 includes a co-pay selection bar 720, and a cost analysis table 730. The co-pay selection bar 720 presents possibly co-pays for various insurance plans for the subject medication. In this case, the co-pays for AMBIEN® and its generic version (Zolpidem) are 5 dollars, 10 dollars, 20 dollars, or thirty dollars.

The cost analysis table 730 presents, for the same dosage of the subject medication and one or more of its generic versions, the cost for purchasing using insurance and the cost for purchasing without insurance. For example, if a user's co-pay is 10 dollars for both AMBIEN® and Zolpidem, and it costs $195.88 for the AMBIEN® and $5.83 for the Zolpidem, it is cheaper to buy Zolpidem without insurance as it less than the 10 dollar co-pay. However, in cases where the co-pay is 5 dollars it would be more cost effective to buy AMBIEN® using insurance—as the 5 dollar co-pay is less than it would be to buy AMBIEN® ($195.88) or Zolpidem ($5.83) without using insurance. Accordingly, a user is able to utilize the cost interface 710 to determine the most cost efficient way to obtain the subject medication or a generic version thereof.

FIG. 8 illustrates another example of a user interface 800 displayed by a user device 105 showing a medication overview webpage 800 according to an embodiment. The user interface 800 includes a main menu 805, an overview section 810, an effects section 815, a demographically filterable interface 820, and a miscellaneous information section 825. The main menu 805 includes a plurality of selectable navigation buttons that allow a user to navigate to other pages associated with a subject medication (e.g., CYMBALTA®). In this embodiment, the navigation buttons include a basics button, a benefits and tradeoffs button, an alternatives button, a reviews button, a side effects and warnings button, a tips button, and drug facts & package insert button. In this example, the user interface 800 presents the medication overview webpage 800 responsive to the selection of the basics button. These buttons provide similar functionality to some of the buttons 232, 234, 236, 238, 240, 242, 244, and 246 described above in relation to FIG. 2. For example, the drug facts & package insert button, if selected, provides a functionality similar to the selection of the package insert button 246. In other embodiments, the main menu 805 may include one or more different navigation buttons than those described herein or may only include a subset of those navigation buttons. Similarly, the functions of the navigation buttons can be distributed and/or among the navigation buttons in a different manner than is described here.

The overview section 810 provides a short description of the subject medication. In some embodiments, the overview section 810 also indicates whether the subject medication is prescription or non-prescription. Additionally, the overview section lists common areas of interest that potentially are affected when taking the subject medication. For example, pregnancy, alcohol, food, kidneys, liver, and sex are common areas of interest that potentially are affected in users of CYMBALTA®. A user is able to select one or more of the common areas of interest, and then receive information specific to the one or more selected common areas of interest by selecting the get results button 830. For example, the user interface 800 shows that "Food" and "Liver" are selected, the other common areas of interest are not selected, and responsive to a selection of the button 830 the user interface 800 presents information (not shown) associated with the selected common areas of interest.

The effects section 815 presents information regarding effects of the subject medication for users who are taking the subject medication to treat a particular condition. The effects section 815 includes a condition menu 835 and a side effects graph 840. The condition menu 835 is a drop down menu that includes one or more possible conditions (e.g., depression, anxiety, etc.). In some embodiments, the condition menu 835 may include an "all uses" condition which aggregates effectiveness information and common side effects information associated with the other conditions available for selection. The side effects graph 840 presents information describing an effectiveness of the subject medication and common side effects of the subject medication. The common side effects information presented by the side effects graph 840 may come from reported side effects of other users of the medication analysis system 125, the survey service provider 115, clinical trial information within the FDA package insert for the subject medication, or some combination thereof. The effectiveness and common side effects information are presented as a function of time since a user of the medication began treatment with the subject medication. For example, for users of CYMBALTA®, treatment of the condition with the CYMBALTA® started working during the "First few weeks" and the "Full effects" were experienced during the "First few months." Similarly, a common side effect of "Drowsiness" was experienced from the "First few hours" all the way through to the "First few weeks" of taking CYMBALTA®.

A user of the user device 105 may also provide feedback that they to experience a particular common side effect associated with taking the subject medication for a particular condition by, e.g., selecting a particular location along one or more of the common side effects. In some embodiments, responsive to the selection the effects section 815 adds an icon (e.g., Me Too icon 845) indicating the area selected by the user. Responsive to the selection, the user device 100 provides the feedback information to the medication analysis system 125. In embodiments, where the user is logged into the medication analysis system 125, the medication analysis system 125 may update a medication profile associated with the user with the feedback information.

The demographically filterable interface 820 presents an overall worth percentage as a function of gender, age, and condition. The interface 820 includes a condition menu 850, a demographic selection area 855, and a results area 860. The condition menu 850 is a drop down menu similar to condition menu 835. The demographic selection area 855 allows a user to select different demographics. In this example, the demographic selection area 855 presents different age ranges to the user. Responsive to a selection of a particular demographic (e.g., "All ages") and a condition (e.g., "All uses"), the medication analysis system 125 determines a percentage of male users who found the subject medication worth it (i.e., a user felt that positives of the subject medication outweighed the negatives) and a percentage of female users who found the subject medication worth it. The medication analysis system 125 then provides the determined percentages to the user device 105 for presentation to the user. In alternate embodiments, the medication analysis system 125 some other measure of user satisfaction (e.g., amount of hassle, effectiveness, etc.) associated with the subject medication, and then provides the determined measure of user satisfaction to the user device 105.

The miscellaneous information section 825 displays various information about the subject medication. The information about the subject medication may be provided to the user interface 800 by, e.g., the medication analysis system 125 and/or the third party database 120. In some embodiments, the information about the subject medication may describe why it is commonly used, how the medication is generally categorized (e.g., opiate, sedative, etc.), how the medication works, a generic name for the medication, brand names for the medication, what the medication is used for, dosage forms, drug class for the medication, possible generic alternatives to the medication, some other information associated with the medication, or some combination thereof.

Medication Analysis System

Figure 9:
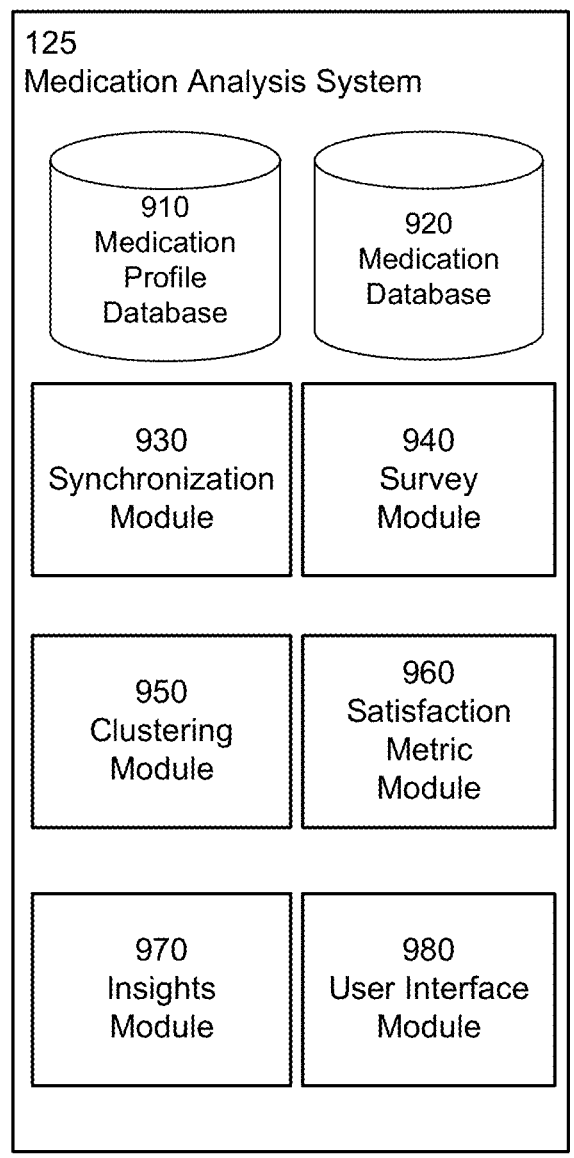
FIG. 9 is a high-level block diagram illustrating a detailed view of the medication analysis system according to one embodiment.

FIG. 9 is a high-level block diagram illustrating a detailed view of the medication analysis system 125 according to one embodiment. The medication analysis system 125 is comprised of modules including a medication profile database 910, a medication database 920, a synchronization module 930, a survey module 940, a clustering module 950, a satisfaction metric module 960, an insights module 970, and a user interface module 980. Some embodiments of the medication analysis system 125 have different modules than those described here or may only include a subset of those modules. Similarly, the functions can be distributed among the modules in a different manner than is described here.

The medication profile database 910 stores medication profiles. A medication profile may be associated with a user of the medication analysis system 125 or some other person who was surveyed by a survey service provider 115. A medication profile includes multiple data fields, each describing one or more attributes of a corresponding person. Examples of information stored in a medication profile include login and password information if they are a user of the medication analysis system 125, survey information including demographic information (e.g., age, gender, etc.), and user experience information (e.g., a tip regarding the medication, measure of satisfaction with the medication, etc.), personal identifying information (e.g., name, address, etc.) for the person, or some combination thereof.

The medication database 920 stores prescription information associated with different medications. The medication database 920 may update its prescription information based on changes to prescription information in, for example, the third party database 120 and/or manual updates received from an administrator.

The synchronization module 930 synchronizes the prescription information stored in the medication database 920 with prescription information in the third party database 120. If a change occurs to prescription information for a medication at the third party database 120, the synchronization module 930 automatically updates the medication database 920 with the change. For example, if a new medication is added to the third party database 120, the synchronization module 930 automatically detects the newly added content, and updates the medication database 920 with prescription information associated with the new medication. Similarly, if prescription information for a particular medication is modified (e.g., add additional adverse effect) the synchronization module 930 automatically detects the change and modifies the corresponding prescription information in the medication database 920 accordingly.

The survey module 940 interacts with one or more survey service providers 115 to obtain responses to medical surveys. In some embodiments, the survey module 940 may generate one or more survey questions to be used in a medical survey which queries Internet users about their experiences with one or more medications (i.e., user experience information) and/or one or more of their demographic characteristics. Alternatively, an administrator of the medication analysis system 125 may provide the one or more survey questions. The survey questions may ask, e.g., whether a user has used a particular medication, how much of a hassle it was to use the medication, the effectiveness of the medication, the length of time the medication was taken, what employment medical insurance plan (including medication coverage) and/or employment dental insurance plan is used by the user, what the user's co-pay was for the medication, what side-effects the user had while on the medication, any tips regarding the use of the medication, was the medication overall worth taking, the user for one or more demographic characteristics about the user, some other question relating to the user's experience with the medication, or some combination thereof.

Additionally, in some embodiments, the survey module 940 and/or the administrator may associate one or more targeting criteria with the survey questions. The survey module 940 provides the survey questions and any targeting criteria to one or more survey service providers 115 who survey targeted users about their experiences with one or more medications using medical surveys generated using the questions. The survey module 940 receives survey information describing user responses to the medical surveys from the one or more service providers 115. The survey module 940 updates the medication profile database with the received survey information.

The clustering module 950 clusters medication profiles into one or more clusters of medication profiles, where each cluster of medication profiles is associated with a different medication. The clustering module 950 identifies medication profiles in the medication profile database 910 that include user experience information describing peoples' experiences with a common (i.e., same) medication, and then generates a cluster of medication profiles using the identified medications profiles. For example, the clustering module 950 may generate a cluster of medication profiles for all medication profiles that include user experience information relating to the medication AMBIEN®. A medication profile may be associated with multiple clusters if the medications profile includes user experience information for different medications. Each medication profile includes demographic information, accordingly, the clusters of medication profiles may be filtered using one or more desired demographic characteristics.

The clustering module 950 may generate clusters periodically (e.g., daily, weekly, etc.), at set times (e.g., set by the administer), after receiving additional survey information, responsive to receiving an instruction from the user interface module 980, or some combination thereof. For example, the clustering module 950 may receive from the user interface module 980 an instruction to generate a cluster about a particular medication.

The satisfaction metric module 960 analyzes the clusters of medication profiles to determine one or more satisfaction metrics for various medications. As noted previously, a satisfaction metric is a measure of one or more medication users' satisfaction with using a medication. Satisfaction metrics may include, e.g., performance distributions, stories about the medication, side effects information for the medication, some other information that indicates that a person was satisfied with the medication, etc. A performance distribution describes reported satisfaction with a particular medication for a given set of medication profiles. A performance distribution may be a distribution that, for example, measures the amount of hassle a set of medication profiles indicated was associated with using a medication, measures the effectiveness of the medication as indicated by the set of medication profiles, measures the overall worth of taking the medication as indicated by the set of medication profiles, etc. A story about the medication includes a user tip about the medication and one or more demographic characteristics of the user. The tip may be structured data, unstructured data, or some combination thereof. An example story is discussed above with reference to stories 482, 484 in FIG. 4B. Side effects information describes side effects experienced by users of the medication. Side effects may include any effects experienced by a user of the medication (e.g., drowsiness, dizziness, allergy, dry mouth, etc.).

The satisfaction metric module 960 determines one or more satisfaction metrics for a medication based on some or all of the medication profiles in a cluster of medication profiles. The satisfaction metrics may be determined for a medication based on an identified set of medication profiles within the cluster. The identified set of medication profiles may be all of the medication profiles in the cluster and/or a group of medication profiles in the cluster having one or more same or similar demographic characteristics (e.g., only male, above 55 years in age, etc.). In general, the identified set may initially be any combination of medication profiles within the cluster. In some embodiments, the identified set is initially determined to be all the medication profiles within the cluster. A user may then later modify what medication profiles are included in the identified set using a filter interface. In other embodiments, the identified set is initially determined to be a group of medication profiles sharing similar demographic characteristics as the user (e.g., same gender and age range), and the user may later modify what medication profiles are included in the identified set using a filter interface.

The satisfaction metric module 960 may generate satisfaction metrics periodically (e.g., daily, weekly, etc.), at set times (e.g., set by the administer), after a new cluster is generated and/or has been updated with additional survey information, responsive to receiving an instruction from the user interface module 980 to update a satisfaction metric, or some combination thereof. For example, in some embodiments, the satisfaction metric module 960 initially determines one or more satisfaction metrics using all of the medication profiles in the cluster. Responsive to receiving an instruction from the user interface module 980 to update a satisfaction metric based on one or more desired demographic characteristics, the satisfaction metric module 960 identifies a set of medication profiles within the cluster having the desired demographic characteristics and provides the updated satisfaction metric to the user interface module 980.

For a given cluster, the satisfaction metric module 960 extracts from each medication profile of the identified set, a portion of the user experience information describing a level satisfaction with the medication. In embodiments where the satisfaction metric module 960 is generating performance distributions and/or extracting side effects information, the satisfaction metric module 960 separates the extracted data by like measures of satisfaction (e.g., effectiveness, hassle, worthwhile, type of side effect, etc.) and generates satisfaction metrics for each measure of satisfaction. For example, for an identified set of medication profiles within a cluster, a performance distribution may indicate that 70% of the identified set of medication profiles indicated that the medication works, 20% of the identified set of medication profiles indicated that the medication worked somewhat, and 10% of the identified set of medication profiles indicated that the medication did not work at all. Similarly, the satisfaction metric module 960 may generate a listing of the most common side effect and less common side effects for the identified medication profiles based on the data extracted from the user experience information of the identified set of medication profiles.

In some embodiments where the satisfaction metric module 960 is extracting side effects information from medication profiles, the side effects information includes one or more types of side effects (e.g., cough, runny nose, drowsiness, etc.). The satisfaction metric module 960 ranks the types of side effects based on a number of occurrences for each type of side effect in the extracted side effects information. The satisfaction metric module 960 generates one or more listings of the side effect types based on the ranking A listing may include, for example, a number of most common side effect types (e.g., top 10 side effect types in the ranking), a listing of least common side effect types (e.g., bottom 10 side effect types in the ranking) In some embodiments, the satisfaction metric module 960 may provide one or more listings of side effects to the user interface module 980 to be included in a demographically filterable interface.

In embodiments, where the satisfaction metric module 960 is generating stories about the medication, the satisfaction metric module 960 selects medication profiles within the identified set of medication profiles that have user experience information including a tip about the medication. The satisfaction metric module 960 then generates a story for each of the selected medication profiles. Each story includes a tip and one or more demographic characteristics about the user. Example stories are discussed above with regard to FIG. 4B.

The insights module 970 develops insights for use of medications using the medication profiles. The insights module 970 conducts and ongoing analysis of the medication profiles to ascertain common behaviors or attributes that certain user segments have in common. The insights module 970 determines correlations, for a given medication, between specific aspects of user experience information reported for the medication, demographic characteristics of users taking the medication, and the effectiveness of the medication. In some embodiments, the insights module 970 may identify a set of medication profiles with user experience information reporting the medication as being highly effective, another set of medication profiles with user experience information reporting the medication as being somewhat effect, and another set of medication profiles with user experience information reporting the medication as being. The insights module 970 may then identify which types of user experience information and demographic characteristics appear within each set of medication profiles. The insights module 970 then may rank the identified types of user experience information and/or demographic information in accordance with the number of times they appear within the sets of medication profiles. The insights module 970 generates insights about the medication using one or more of the highest ranked types of user experience information and/or demographic characteristics for each of the sets. For instance, people who rate a medication as "not worth it" (not effective/a lot of hassle) might commonly be pregnant women, or people who rate a medication as "not worth it" (not effective/much hassle) might all have been taking it for a year or longer, etc. The insights module 970 provides insights to the user interface module 980.

The user interface module 980 presents one or more graphical user interfaces (GUIs) to the user of the user device 105. The GUIs allow a user to interact with the medication analysis system 125. In some embodiments, one or more of the GUIs may include one or more insights about a medication. The GUIs may include demographically filterable interfaces. A demographically filterable interface is a user interfaces which presents one or more satisfaction metrics for a medication to a user as a function of one or more selectable demographic characteristics of the users' of the medication. For example, a demographically filterable interface may include selectable buttons allowing a user to choose a desired demographic makeup of the medication users whose medication profiles are used to generate the satisfaction metrics. In some embodiments, the selectable buttons are part of a demographic filter as discussed above with regard to FIGS. 2, 3A-B, 4A-B, and 5.

The user interface module 980 generates a homepage that is presented to a user of a user device 105 via, e.g., a browser. The user interface module 980 receives from a user device 105 an input from a user that requests information about a particular medication (subject medication). For example, a user may request information on the medication AMBIEN®. Responsive, to receiving the input requesting information on the subject medication, the user interface module 980 generates a medication overview webpage for the subject medication that includes a demographically filterable interface and provides the medication overview page to the user device 105. An example medication overview webpage for the medication, AMBIEN®, is described above with reference to FIG. 2.

A user may navigate to different webpages using navigation buttons. Responsive to receiving an instruction from the user device 105 that a particular navigation button (e.g., tradeoffs button 234, side effects button 238, etc.) has been selected, the user interface module 980 generates a user interface that presents a webpage that corresponds to the selected navigation button and provides the user device 105 with the generated user interface.

For example, responsive to the selection of the tradeoff button 234, the user interface module 980 generates the webpage shown in FIG. 3A. The user interface module 980 retrieves prescription information associated with the medication from the medication database 920. The user interface module 980 identifies one or more alternative medications using the retrieved prescription information. The user interface module 980 then instructs the clustering module 950 to identify one or more clusters of medication profiles in the medication profile database 910 that include user experience information describing experiences with the alternative medications. The user interface module 980 instructs the satisfaction metric module 960 to identify a set of medication profiles within each cluster that have demographic information that matches a desired demographic of users of the medication. The user interface module 980 also instructs the satisfaction metric module 960 to determine one or more satisfaction metrics for each of the alternative medications using user experience information in the identified sets of medication profiles. The user interface module 980 also instructs the satisfaction metric module 960 to generate the demographically filterable interface such that the satisfaction metrics for the alternative medications are presented relative to a level of satisfaction for the medication.

In some embodiments, one or more webpages presented by the user interface include demographically filterable interfaces (e.g., 215, 310, 410, 465, and 550). Information used to generate a demographically filterable interface is obtained from the satisfaction metric module 960. Additionally, in some embodiments, the user interface module 980 may receive a request to filter, by one or more desired demographic characteristics (e.g., age and gender), a satisfaction metric (e.g., performance distributions, stories, side effects information, etc.) presented via the demographically filterable interface. The user interface module 980 instructs the satisfaction metric module 960 to update the satisfaction metric based on the desired demographic makeup of medication users. The user interface module 960 receives the updated satisfaction metric from the satisfaction metric module 960, and updates the demographically filterable interface with the updated satisfaction metric. Accordingly, a user interacting with the demographically filterable interfaces is able to actively filter the information being presented using one or more demographic characteristics, thus allowing a user to better see how a subject medication affects users having the same or similar demographic characteristics as the user.

The user interface module 980 also generates other interfaces based in part on prescription information. In embodiments, where the side effects button is selected, the user interface module 980 generates a clinical interface element (e.g., clinical interface element 510 in FIG. 5) that presents the common side effects reported during clinical trials as a function of a condition being treated by the subject medication. The user interface module 980 generates the clinical interface element using prescription information for the subject medication in the medication database 920. Similarly, in embodiments, where the real life button, the warnings button, the cost button, the FAQ button, or the package insert is selected, the user interface module 980 retrieves information used to generate the appropriate interface using prescription information associated with the subject medication.

For example, in embodiments where the cost button is selected, the user interface module 980 generates an interface that may be used to determine whether buying a medication or a generic version of the medication using insurance, or not using insurance, would save the user money. The user interface module 980 retrieves information from the prescription information identifying one or more alternative medication (e.g., a generic version). Additionally, the user interface module 980 retrieves from the medication profiles information identifying the amounts paid by users without insurance for the medication and any identified alternative medications. The user interface module 980 obtains from the prescription information and/or the medication profiles the amounts paid by users with insurance for the medication and any identified alternative medications. The user interface module 980 determines what medication (the medication or an alternative medication) is cheapest to purchase and how that medication should be purchased (with or without using insurance) as a function of the co-pay of the user. In some embodiments, the user interface module 980 emphasizes the identified medication in the user interface. The user interface module 980 then provides the interface to the user device 105. A user is able to select a different co-pay, and the user interface module 980 re-determines which medication is cheapest to purchase and how that medication should be purchased given the different co-pay, and updates the interface provided to the user device 105 accordingly.

Responsive to receiving a selection of a review button on an interface generated by the user interface module 980, the user interface module 980 presents a form interface to the user asking for some demographic information about the user and some user experience information that describes that user's experiences with the subject medication. For example, the form interface may request age of the user, gender of the user, a brief description of the user (e.g., How would you describe yourself?), information describing why the user is taking the subject medication, a length of time the user has been taking the subject medication, some other demographic information, some other information describing the user's experience with the subject medication, or some combination thereof. The information received from the user via the form interface is stored by the user interface module 980 in the medication profile database 910 as a medication profile associated with the user. In some embodiments, where a user already has an existing medication profile, the user interface module 980 updates the existing medication profile with the received information.

Figure 10:
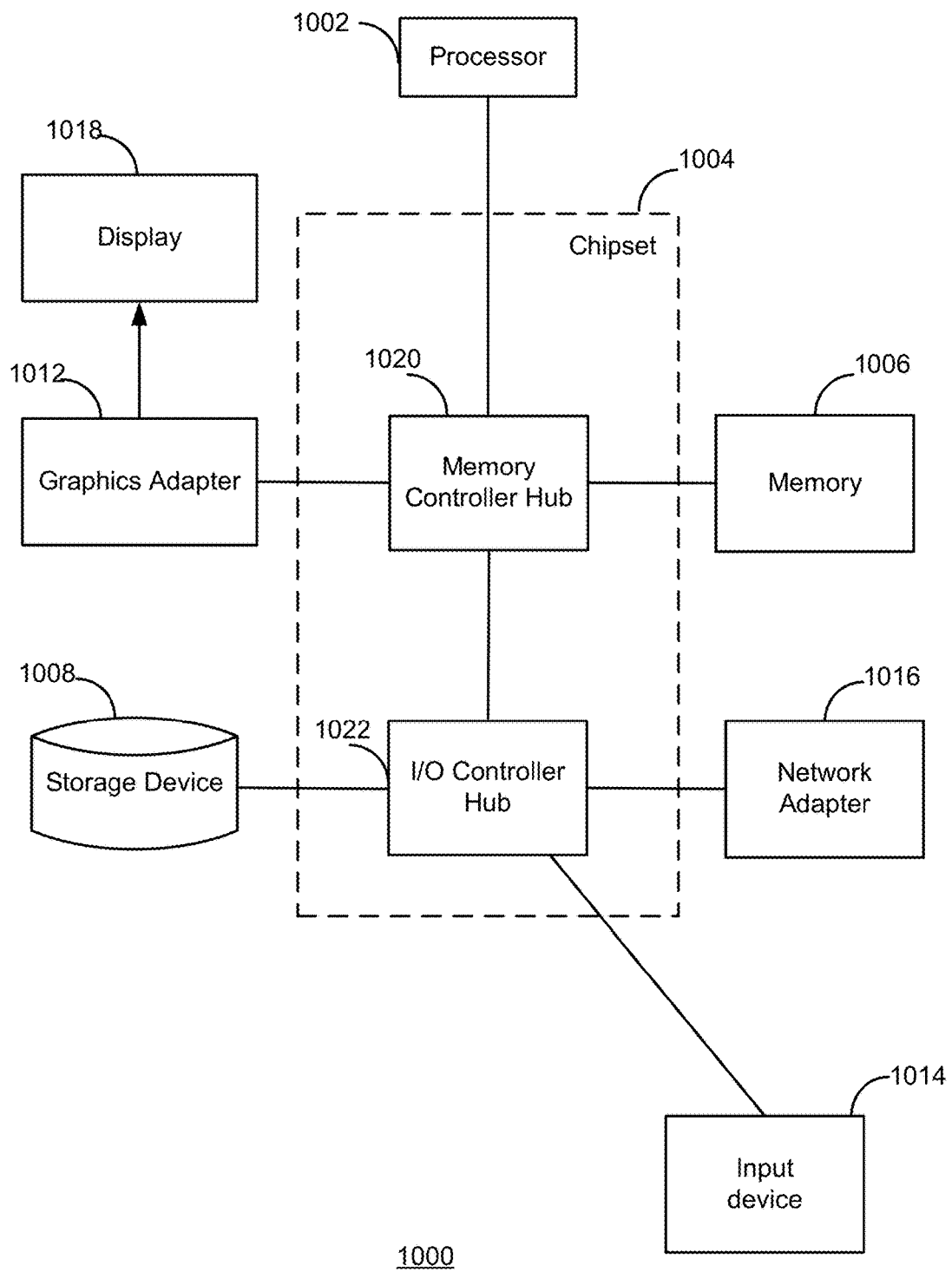
FIG. 10 is a high-level block diagram illustrating an example computer.

Turning now to a discussion of the implementation of user device 105, the survey service provider 115, the third party database 120, and/or the medication analysis system 125, FIG. 10 is a block diagram illustrating an example computer 1000 for implementing the entities shown in FIG. 1. The computer 1000 includes at least one processor 1002 coupled to a chipset 1004. The chipset 1004 includes a memory controller hub 1020 and an input/output (I/O) controller hub 1022. A memory 1006 and a graphics adapter 1012 are coupled to the memory controller hub 1020, and a display 1018 is coupled to the graphics adapter 1012. A storage device 1008, an input device 1014, and network adapter 1016 are coupled to the I/O controller hub 1022. Other embodiments of the computer 1000 have different architectures.

The storage device 1008 is a non-transitory computer-readable storage medium such as a hard drive, compact disk read-only memory (CD-ROM), DVD, or a solid-state memory device. The memory 1006 holds instructions and data used by the processor 1002. The input interface 1014 is a touch-screen interface, a mouse, track ball, or other type of pointing device, a keyboard, or some combination thereof, and is used to input data into the computer 1000. In some embodiments, the computer 1000 may be configured to receive input (e.g., commands) from the input interface 1014 via gestures from the user. The graphics adapter 1012 displays images and other information on the display 1018. The network adapter 1016 couples the computer 1000 to one or more computer networks.

The computer 1000 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 1008, loaded into the memory 1006, and executed by the processor 1002.

The types of computers 1000 used by the entities of FIG. 1 can vary depending upon the embodiment and the processing power required by the entity. In some embodiments, the user device 105 may interact with one or more servers working together to provide the functionality described herein. For example, the medication analysis system 125 may include multiple computers 1000 communicating with each other through a network such as in a server farm to provide the functionality described herein. The computers 1000 can lack some of the components described above, such as graphics adapters 1012, and displays 1018.

Generating an Demographically Filterable Interface

Figure 11:
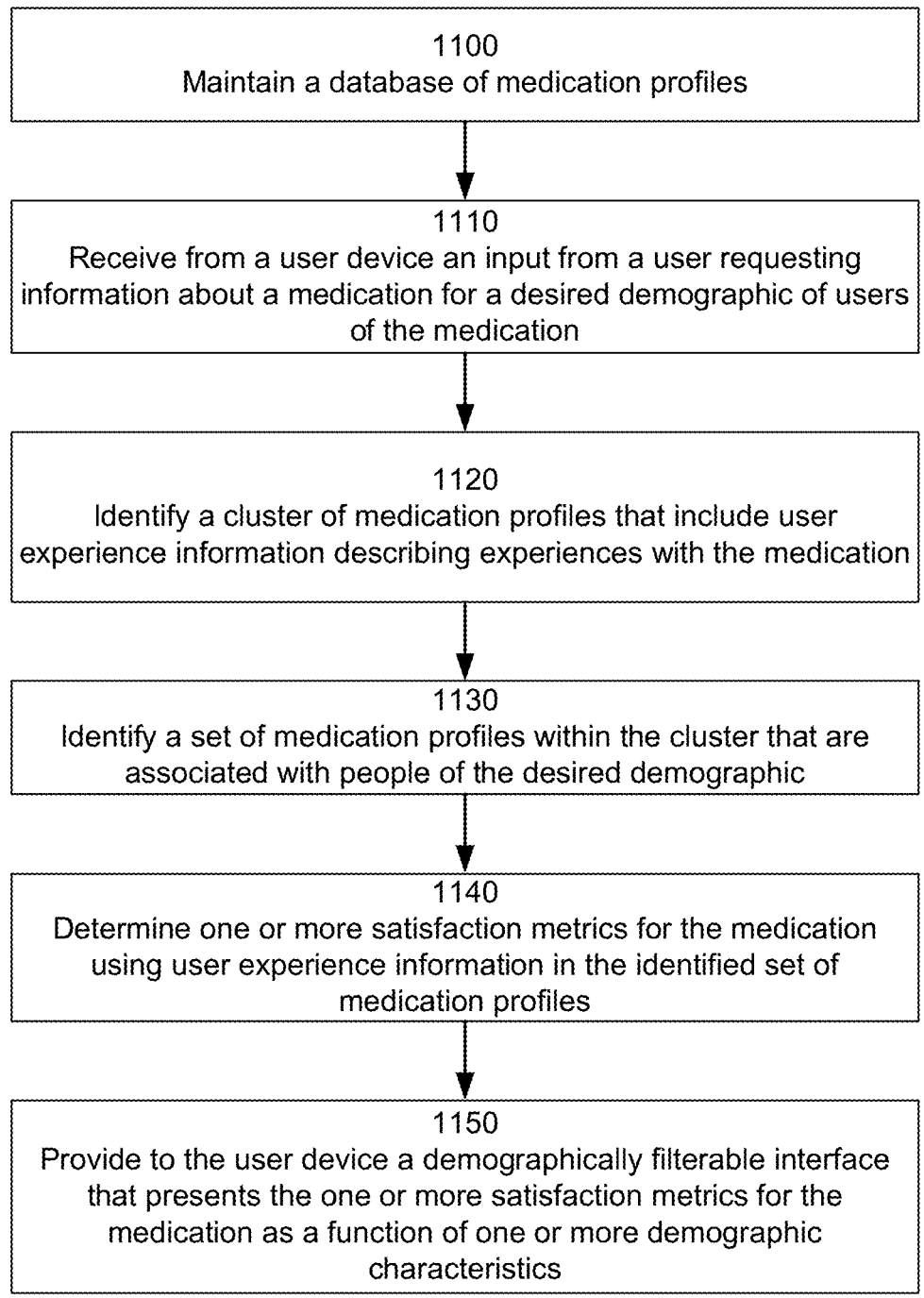
FIG. 11 is a flowchart illustrating the process of generating a demographically filterable interface according to one embodiment.

FIG. 11 is a flowchart illustrating the process of generating a demographically filterable interface according to one embodiment. In one embodiment, the process of FIG. 11 is performed by the medication analysis system 125. Other entities may perform some or all of the steps of the process in other embodiments. Likewise, embodiments may include different and/or additional steps, or perform the steps in different orders.

The medication analysis system 125 maintains 1100 a database of medication profiles (e.g., the medication profile database 910). The medication analysis system 125 receives 1110 from a user device 105 an input from a user requesting information about a medication for a desired demographic of users of the medication. The desired demographic may be all users of the medication with associated medication profiles or a subset of users having one or more common demographic characteristics (e.g., age, gender, etc.) and associated medication profiles.

The medication analysis system 125 identifies 1120 a cluster of medication profiles that include user experience information describing experiences with the medication. In some embodiments, the medication analysis system 125 identifies medication profiles in the medication profile database 910 that include user experience information describing peoples' experiences with a common (i.e., same) medication, and then generates a cluster of medication profiles using the identified medications profiles. Alternatively, the medication analysis system 125 may identify a previously generated cluster of medication profiles that include user experience information describing experiences with the medication.

The medication analysis system 125 identifies 1130 a set of medication profiles within the cluster that are associated with people of the desired demographic. The identified set of medication profiles may be all of the medication profiles in the cluster and/or a group of medication profiles in the cluster having at least one same or similar demographic characteristics (e.g., only male, above 55 years in age, etc.). In some embodiments, the identified set of medication profiles are those that share one or more similar demographic characteristics of the user (e.g., same age range and gender).

The medication analysis system 125 determines 1140 one or more satisfaction metrics for the medication using user experience information in the identified set of medication profiles. The medication analysis system 125 extracts from each medication profile of the identified set, a portion of the user experience information describing the medication user's satisfaction with the medication. In embodiments, where the one or more satisfaction metrics include performance distributions and/or side effects information, the medication analysis system 125 separates the extracted data by like measures of satisfaction (e.g., effectiveness, hassle, worthwhile, reported side effects, etc.) and generates satisfaction metrics for each measure of satisfaction. In embodiments, where the satisfaction metric includes one or more stories, the medication analysis system 125 selects medication profiles within the identified set of medication profiles that have user experience information including a tip about the medication, and generates a story for each of the selected medication profiles.

The medication analysis system 125 provides 1150 to the user device 105 a demographically filterable interface that presents the one or more satisfaction metrics for the medication as function of one or more demographic characteristics.

Additional Configuration Considerations

Some portions of the above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality. The described operations and their associated modules may be embodied in software, firmware, hardware, or any combinations thereof.

As used herein any reference to "one embodiment" or "an embodiment" means that a particular element, media feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

Upon reading this disclosure, those of skill in the art will appreciate still additional alternative structural and functional designs for a system and a process for analyzing effects of medications on users of varying demographic backgrounds and presenting results of the analysis to users using demographic filterable interfaces that allow users to filter the results presented using one or more demographic characteristics. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the method and apparatus disclosed herein.

What is claimed is:

1. A method comprising:
   maintaining a database of medication profiles for users of medications, each medication profile being associated with a person and including demographic information about the person and user experience information describing the person's experiences with one or more medications, wherein the database is generated based in part on demographic information and user experience information directly provided by some of the users of medications;
   receiving from a user device an input from a user that is a patient, the input requesting information about a subject medication for a desired demographic of users of the subject medication;
   identifying a cluster of medication profiles from the database of medication profiles that include user experience information describing experiences with the subject medication;
   identifying a set of medication profiles within the cluster that have demographic information that matches the desired demographic;
   determining one or more satisfaction metrics for the subject medication using user experience information in the identified set of medication profiles, wherein a satisfaction metric is a measure of one or more users' satisfaction with using a medication;
   providing to the user device an overview webpage for the subject medication, the overview webpage comprising a plurality of navigation buttons to navigate to a set of secondary webpages, the plurality of navigation buttons including a tradeoffs button;
   responsive to the selection of the tradeoff button of the navigable buttons, generating a tradeoff webpage that includes a demographically filterable interface that includes a graph that presents the one or more satisfaction metrics for the subject medication as a function of one or more demographic characteristics of the demographic information of the people associated with the identified medication profiles, and a demographic filter that allows the user to filter data presented by the graph by at least some of the one or more demographic characteristics, the graph plotting a representation for each of the subject medication and one or more alternative medications as a function of two different satisfaction metrics of the determined satisfaction metrics, and the subject medication is positioned at a center of the graph and the alternative medications are positioned relative to the subject medication; and
   providing to the user device the tradeoff webpage.

2. The method of claim 1, further comprising:
   generating an insight for the effectiveness of the subject medication using the user experience information and the demographic information of the identified set of medication profiles.

3. The method of claim 1, wherein the satisfaction metrics are selected from a group comprising: a performance distribution relating to hassle of taking the subject medication, a performance distribution relating to the effectiveness of the subject medication, a performance distribution relating to the overall worth of taking the subject medication, one or more stories about the medication, and side effects information for the subject medication.

4. The method of claim 1, further comprising:
   responsive to the selection of an medication basics button of the navigable buttons, generating the overview webpage, and the overview webpage includes a demographically filterable interface that presents the one or more satisfaction metrics for the subject medication as a function of one or more demographic characteristics of the demographic information of the patients associated with the identified medication profiles, and the one or more satisfaction metrics are a performance distribution relating to hassle of taking the subject medication, a performance distribution relating to the effectiveness of the subject medication, and a performance distribution relating to the overall worth of taking the subject medication; and
   providing to the user device the overview webpage.

5. The method of claim 1, wherein the tradeoff webpage presents information describing how people feel about the subject medication when compared to alternatives, the method further comprising:
   identifying an alternative medication using prescription information associated with the subject medication;
   identifying a cluster of medication profiles from the database of medication profiles that include user experience information describing experiences with the alternative medication;

identifying a set of medication profiles within the cluster that have demographic information that matches the desired demographic; and determining one or more satisfaction metrics for the alternative medication using user experience information in the identified set of medication profiles.

6. The method of claim 1, further comprising:

responsive to a selection of a real life button, generating a real life webpage that presents information describing peoples' experiences with the subject medication outside of a clinical context, and the real life webpage includes a demographically filterable interface that presents the one or more satisfaction metrics for the subject medication as a function of one or more demographic characteristics of the demographic information of the patients associated with the identified medication profiles and the one or more satisfaction metrics are each a performance distribution relating to hassle of taking the medication and a performance distribution relating to the effectiveness of the subject medication, and the performance distributions are presented in a grid including a plurality of sections, wherein each section of the grid is associated with an amount of hassle and an amount of effectiveness; and providing to the user device the real life webpage.

7. The method of claim 1, further comprising:

responsive to a selection of a real life button, generating a real life webpage that presents information describing peoples' experiences with the subject medication outside of a clinical context, and the real life webpage includes a demographically filterable interface that presents the one or more satisfaction metrics for the subject medication and the one or more satisfaction metrics are a plurality of stories, the method further comprising:

selecting medication profiles within the identified set of medication profiles that have user experience information including a tip about the subject medication; and generating a story for each of the selected medication profiles, each story including a tip and one or more demographic characteristics from the corresponding selected medication profile; and providing to the user device the real-life webpage.

8. The method of claim 1, further comprising:

responsive to a selection of a side effect button, generating a side effects webpage, and the side effects page includes a demographically filterable interface, and the one or more satisfaction metrics include side effects information, the method further comprising:

extracting side effects information from medication profiles in the identified set of medication profiles, the side effects information including one or more types of side effects;

ranking the types of side effects based on the number each type of side effect occurs in the extracted side effects information;

generating a listing of side effects based on the ranking; and providing to the user device the side effects webpage.

9. The method of claim 1, further comprising:

providing a review button to the user device for display as part of an interface including the demographically filterable interface;

responsive to receiving a selection of the review button, generating a form interface asking for some demographic information about the user and some user experience information describing the user's experiences with the subject medication;

storing information received from the form interfaces as a medication profile in the database of medication profiles; and adding an indicator to a satisfaction metric, of the one or more satisfaction metrics, the indicator reflecting where the user falls within the information described by the satisfaction metric.

10. A non-transitory computer-readable storage medium storing executable computer program instructions, the instructions executable to perform steps comprising:

maintaining a database of medication profiles for users of medications, each medication profile being associated with a person and including demographic information about the person and user experience information describing the person's experiences with one or more medications, wherein the database is generated based in part on demographic information and user experience information directly provided by some of the users of medications;

receiving from a user device an input from a user that is a patient, the input requesting information about a subject medication for a desired demographic of users of the subject medication;

identifying a cluster of medication profiles from the database of medication profiles that include user experience information describing experiences with the subject medication;

identifying a set of medication profiles within the cluster that have demographic information that matches the desired demographic;

determining one or more satisfaction metrics for the subject medication using user experience information in the identified set of medication profiles, wherein a satisfaction metric is a measure of one or more users' satisfaction with using a medication;

providing to the user device an overview webpage for the subject medication, the overview webpage comprising a plurality of navigation buttons to navigate to a set of secondary webpages, the plurality of navigation buttons including a tradeoffs button; and responsive to the selection of the tradeoff button of the navigable buttons, generating a tradeoff webpage that includes a demographically filterable interface that includes a graph that presents the one or more satisfaction metrics for the subject medication as a function of one or more demographic characteristics of the demographic information of the patients associated with the identified medication profiles, and a demographic filter that allows the user to filter data presented by the graph by at least some of the one or more demographic characteristics, the graph plotting a representation for each of the subject medication and one or more alternative medications as a function of two different satisfaction metrics of the determined satisfaction metrics, and the subject medication is positioned at a center of the graph and the alternative medications are positioned relative to the subject medication; and providing to the user device the tradeoff webpage.

11. The computer-readable medium of claim 10, further comprising:

generating an insight for the effectiveness of the subject medication using the user experience information and the demographic information of the identified set of medication profiles.

12. The computer-readable medium of claim 10, wherein the satisfaction metrics are selected from a group comprising: a performance distribution relating to hassle of taking the subject medication, a performance distribution relating to the effectiveness of the subject medication, a performance distribution relating to the overall worth of taking the subject medication, one or more stories about the medication, and side effects information for the subject medication.

13. The computer-readable medium of claim 10, further comprising:
responsive to the selection of an medication basics button of the navigable buttons, generating the overview webpage, and the overview webpage includes a demographically filterable interface that presents one or more satisfaction metrics for the subject medication as a function of one or more demographic characteristics of the demographic information of the patients associated with the medication profiles, and the one or more satisfaction metrics are a performance distribution relating to hassle of taking the subject medication, a performance distribution relating to the effectiveness of the subject medication, and a performance distribution relating to the overall worth of taking the subject medication, and
providing to the user device the overview webpage.

14. The computer-readable medium of claim 10, wherein the tradeoff webpage presents information describing how people feel about the subject medication when compared to alternatives, the method further comprising:
identifying an alternative medication using prescription information associated with the subject medication;
identifying a cluster of medication profiles from the database of medication profiles that include user experience information describing experiences with the alternative medication;
identifying a set of medication profiles within the cluster that have demographic information that matches the desired demographic;
determining one or more satisfaction metrics for the alternative medication using user experience information in the identified set of medication profiles.

15. The computer-readable medium of claim 10, further comprising:
responsive to a selection of a real life button, generating a real life webpage that presents information describing people's experiences with the subject medication outside of a clinical context, and the real life webpage includes a demographically filterable interface that presents the one or more satisfaction metrics for the subject medication as a function of one or more demographic characteristics of the demographic information of the patients associated with the identified medication profiles and the one or more satisfaction metrics are each a performance distribution relating to hassle of taking the medication and a performance distribution relating to the effectiveness of the subject medication, and the performance distributions are presented in a grid including a plurality of sections, wherein each section of the grid is associated with an amount of hassle and an amount of effectiveness; and
providing to the user device the real life webpage.

16. The computer-readable medium of claim 10, further comprising:
responsive to a selection of a real life button, generating a real life webpage demographically filterable interface is part of a real life webpage that presents information describing people's experiences with the subject medication outside of a clinical context, and the real life webpage includes a demographically filterable interface that presents the one or more satisfaction metrics for the subject medication and the one or more satisfaction metrics are a plurality of stories, the method further comprising:
selecting medication profiles within the identified set of medication profiles that have user experience information including a tip about the subject medication; and
generating a story for each of the selected medication profiles, each story including a tip and one or more demographic characteristics from the corresponding selected medication profile; and
providing to the user device the real life webpage.

17. The computer-readable medium of claim 10, further comprising:
responsive to a selection of a side effect button, generating a side effects webpage and the side effects page includes a demographically filterable interface is part of a side effects webpage, and the one or more satisfaction metrics include side effects information, the method further comprising:
extracting side effects information from medication profiles in the identified set of medication profiles, the side effects information including one or more types of side effects;
ranking the types of side effects based on the number each type of side effect occurs in the extracted side effects information;
generating a listing of side effects based on the ranking; and
providing to the user device the side effects webpage.

18. The computer-readable medium of claim 10, further comprising:
providing a review button to the user device for display as part of an interface including the demographically filterable interface;
responsive to receiving a selection of the review button, generating a form interface asking for some demographic information about the user and some user experience information describing user's experiences with the subject medication;
storing information received from the form interfaces as a medication profile in the database of medication profiles; and
adding an indicator to a satisfaction metric, of the one or more satisfaction metrics, the indicator reflecting where the user falls within the information described by the satisfaction metric.

19. A system comprising:
a processor configured to execute modules; and
a memory storing the modules, the modules comprising:
a medication profile database configured to maintain a database of medication profiles for users of medications, each medication profile being associated with a person and including demographic information about the person and user experience information describing the person's experiences with one or more medications, wherein the database is generated based in part on demographic information and user experience information directly provided by some of the users medications;
a user interface configured to receive from a user device an input from a user that is a patient, the input requesting information about a subject medication for a desired demographic of users of the subject medication;

a clustering module configured to identify a cluster of medication profiles from the database of medication profiles that include user experience information describing experiences with the subject medication;

a satisfaction metric module configured to:
 identify a set of medication profiles within the cluster that have demographic information that matches the desired demographic; and
 determine one or more satisfaction metrics for the subject medication using user experience information in the identified set of medication profiles, wherein a satisfaction metric is a measure of one or more users' satisfaction with using a medication; and wherein the user interface module is further configured to provide to the user device an overview webpage for the subject medication comprising a plurality of navigation buttons to navigate to a set of secondary webpages, the plurality of navigation buttons including a tradeoffs button, and, in response to the selection of the tradeoff button, a tradeoff webpage that includes a demographically filterable interface that includes a graph that presents the one or more satisfaction metrics for the subject medication as a function of one or more demographic characteristics of the demographic information of the people associated with the identified medication profiles, and a demographic filter that allows the user to filter data presented by the graph by at least some of the one or more demographic characteristics, the graph plotting a representation for each of the subject medication and one or more alternative medications as a function of two different satisfaction metrics of the determined satisfaction metrics, and the subject medication is positioned at a center of the graph and the alternative medications are positioned relative to the subject medication.

20. The system of claim 19, further comprising an insights module configured to generate an insight for the effectiveness of the subject medication using the user experience information and the demographic information of the identified set of medication profiles.

\* \* \* \* \*

UNITED STATES PATENT AND TRADEMARK OFFICE
CERTIFICATE OF CORRECTION

PATENT NO. : 10,073,951 B2  
APPLICATION NO. : 14/746020  
DATED : September 11, 2018  
INVENTOR(S) : Mohebbi et al.

Page 1 of 1

It is certified that error appears in the above-identified patent and that said Letters Patent is hereby corrected as shown below:

In the Claims

Column no: 24, Line(s): 10, Claim 1: "navigable buttons," to read as -- navigation buttons, --

Column no: 24, Line(s): 44, Claim 4: "navigable buttons," to read as -- navigation buttons, --

Column no: 25, Line(s): 55, Claim 8: "on the number" to read as -- on a number of times --

Column no: 26, Line(s): 44, Claim 10: "navigable buttons," to read as -- navigation buttons, --

Column no: 27, Line(s): 12, Claim 13: "navigable buttons," to read as -- navigation buttons, --

Column no: 27, Line(s): 66, Claim 16: "is part of" to read as -- as part of --

Column no: 28, Line(s): 21, Claim 17: "is part of" to read as -- as part of --

Column no: 28, Line(s): 29, Claim 17: "on the number" to read as -- on a number of times --

Signed and Sealed this  
Fourteenth Day of May, 2019

Andrei Iancu  
*Director of the United States Patent and Trademark Office*